United States Patent
Baxter et al.

(10) Patent No.: US 11,401,266 B2
(45) Date of Patent: Aug. 2, 2022

(54) PROCESS FOR THE PREPARATION OF AN OREXIN RECEPTOR ANTAGONIST

(71) Applicants: Merck Sharp & Dohme Corp., Rahway, NJ (US); Merck Sharp & Dohme (UK) Ltd., Hertfordshire (GB)

(72) Inventors: Carl A. Baxter, London (GB); Faye Sheen, Hoddesdon (GB)

(73) Assignee: Merck Sharp & Dohme (UK) Ltd., Hertfordshire (GB)

( * ) Notice: Subject to any disclaimer, the term of this patent is extended or adjusted under 35 U.S.C. 154(b) by 1206 days.

(21) Appl. No.: 14/801,424

(22) Filed: Jul. 16, 2015

(65) Prior Publication Data

US 2021/0309650 A1 Oct. 7, 2021

Related U.S. Application Data

(63) Continuation of application No. 14/002,221, filed as application No. PCT/US2012/026691 on Feb. 27, 2012, now Pat. No. 9,108,959.

(60) Provisional application No. 61/448,814, filed on Mar. 3, 2011.

(51) Int. Cl.
| | |
|---|---|
| *A61K 31/551* | (2006.01) |
| *C07D 249/06* | (2006.01) |
| *C07D 413/04* | (2006.01) |
| *C07D 413/14* | (2006.01) |
| *A61K 31/55* | (2006.01) |

(52) U.S. Cl.
CPC ............ *C07D 413/14* (2013.01); *A61K 31/55* (2013.01); *C07D 249/06* (2013.01); *C07D 413/04* (2013.01)

(58) Field of Classification Search
CPC .. A61K 31/551; C07D 249/06; C07D 413/04; C07D 413/14
See application file for complete search history.

(56) References Cited

U.S. PATENT DOCUMENTS

| | | | |
|---|---|---|---|
| 3,222,359 A | 12/1965 | Reeder et al. | |
| 7,951,797 B2 | 5/2011 | Breslin et al. | |
| 9,108,959 B2 | 8/2015 | Baxter et al. | |
| 9,969,725 B2 | 5/2018 | Mcnevin | |
| 10,030,010 B2 | 7/2018 | Barth | |
| 10,618,891 B2 | 4/2020 | Lin | |
| 2008/0013490 A1 | 1/2008 | Laroia et al. | |
| 2008/0132490 A1* | 6/2008 | Bergman | A61P 3/04 514/218 |
| 2009/0124603 A1 | 5/2009 | Brashear et al. | |
| 2009/0187028 A1 | 7/2009 | Ku et al. | |
| 2019/0040052 A1 | 2/2019 | Lin | |
| 2019/0276414 A1 | 9/2019 | Comely et al. | |

OTHER PUBLICATIONS

Baxter et al., The First Large-Scale synthesis of MK-4305: A Dual Orexin Receptor Antagonist for the Treatment of Sleep Disorder, Organic Process and Research & Development, 2011, 367-375, vol. 15 No. 2.
Carl R. Hopkins, ACS Chemical Neuroscience Molecule Spotlight on Suvorexant, ACS Chem. Neuroscience, 2012, 647-648, 3.
Cox, et al., "Discovery of the Dual Orexin Receptor Antagonist [(7R)-4-(5-Chloro-1,3-benzoxazol-2-yl)-7-methyl-1,4diazepan . . . ", J. Med. Chem, 2010, 5320-5332, vol. 53, No. 14.
Girardin, Convergent Kilogram-Scale Synthesis of Dual Orexin Receptor Antagonist, Organic Process Research & Development, 2012, 61-68, 17.
I. Mangion et al., Enantioselective Synthesis of a Dual Orexin Receptor Antagonist, Org. Letters, 2012, 3458-3461, 14(13).
Radi, Suvorexant, Drugs of the Future, 2013, 27-36, 38(1).
Strotman et al., Reaction Development and Mechanistic Study of a Ruthenium Catalyzed Intramolecular Asymmetric Reductive Amination en Route to the Dual Orexin Inhibitor Suvorexant (MK-4305), Am. Chem. Soc., 2011, pp. 8362-8371, vol. 133, No. 21.
Sullivan, Update on Emerging Drugs for Insomia, Expert Opin. Emerging Drugs, 2012, 295-298, 17(3).

\* cited by examiner

*Primary Examiner* — Brenda L Coleman
(74) *Attorney, Agent, or Firm* — Dianne Pecorano; John C. Todaro

(57) ABSTRACT

The present invention is directed to processes for preparing a diazepane compound which is an antagonist of orexin receptors, and which is useful in the treatment or prevention of neurological and psychiatric disorders and diseases in which orexin receptors are involved. The present invention is further directed to crystalline forms of this diazepane compound and pharmaceutical compositions thereof.

3 Claims, 6 Drawing Sheets

PROCESS FOR THE PREPARATION OF AN OREXIN RECEPTOR ANTAGONIST

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behavior (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A and the orexin-2 receptor (OX2 or OX2R) is capable to bind OX-A as well as OX-B. The physiological actions in which orexins are presumed to participate are thought to be expressed via one or both of OX 1 receptor and OX 2 receptor as the two subtypes of orexin receptors.

Orexin receptors are found in the mammalian brain and may have numerous implications in pathologies such as depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, and obesity; addictive feeding behaviors; binge/purge feeding behaviors; cardiovascular diseases; diabetes; appetite/taste disorders; emesis, vomiting, nausea; asthma; cancer; Parkinson's disease; Cushing's syndrome/disease; basophile adenoma; prolactinoma; hyperprolactinemia; hypophysis tumour/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; conditions associated with visceral pain such as irritable bowel syndrome, and angina; migraine; urinary bladder incontinence e.g. urge incontinence; tolerance to narcotics or withdrawal from narcotics; sleep disorders; sleep apnea; narcolepsy; insomnia; parasomnia; jet lag syndrome; and neurodegenerative disorders including nosological entities such as disinhibition-dementia-parkinsonism-amyotrophy complex; pallido-ponto-nigral degeneration; epilepsy; seizure disorders and other diseases related to general orexin system dysfunction.

The compound of the formula I:

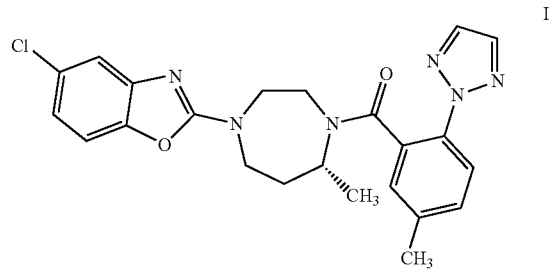 [SMILES: Cc1ccc(-n2nccn2)c(C(=O)N2CCN(c3nc4cc(Cl)ccc4o3)CC[C@H]2C)c1]

is disclosed as an antagonist of orexin receptors in US Patent Application Publication US 2008/0132490, PCT Patent Publication WO 2008/069997 and Cox et al., J. Med. Chem. 2010, 53, 5320-5332. This compound may be named as "5-chloro-2-{(5R)-5-methyl-4-[5-methyl-2-(2H-1,2,3-triazol-2-yl)benzoyl]-1,4-diazepan-1-yl}-1,3-benzoxazole," "[(R)-4-(5-chloro-benzooxazol-2-yl)-7-methyl-[1,4]diazepan-1-yl]-(5-methyl-2-[1,2,3]triazol-2-yl-phenyl)-methanone" or "[(7R)-4-(5-chloro-1,3-benzoxazol-2-yl)-7-methyl-1,4-diazepan-1-yl][5-methyl-2-(2H-1,2,3-triazol-2-yl)phenyl]methanone."

SUMMARY OF THE INVENTION

The present invention is directed to processes for preparing a diazepane compound which is an antagonist of orexin receptors, and which is useful in the treatment or prevention of neurological and psychiatric disorders and diseases in which orexin receptors are involved. The present invention is further directed to crystalline forms of this diazepane compound and pharmaceutical compositions thereof.

DETAILED DESCRIPTION OF THE INVENTION

Figure 1:
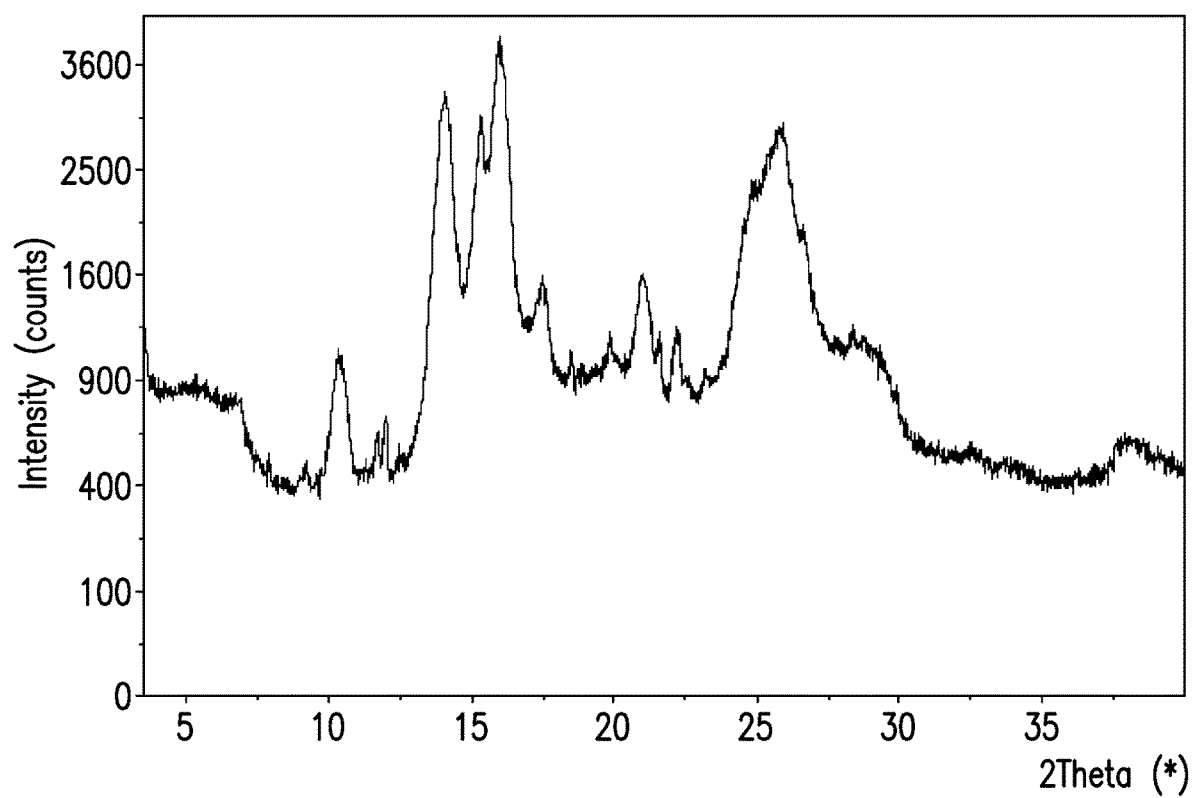
FIG. 1 shows an X-ray diffraction pattern of anhydrous Form I of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone.

The present invention is directed to a process for preparing a compound of the formula I:

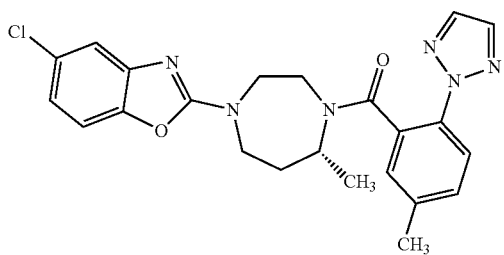

I or a pharmaceutically acceptable salt thereof,
which comprises:
contacting a compound of the formula II:

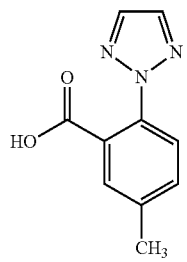

II with an activating agent to form the acid chloride,
followed by contacting the acid chloride with a compound of the formula III:

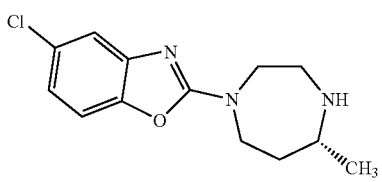

III or a salt thereof,
in the presence of a weak base to give the compound of the formula I, or a pharmaceutically acceptable salt thereof.

In an embodiment of the present invention, the activating agent is selected from oxalyl chloride, thionyl chloride, POCl$_3$, pivaloyl chloride, benzyl chloroformate, CDI, EDC, DCC, HOBt, HOAt, T3P, and HAUT. In an embodiment of the present invention, the activating agent is selected from oxalyl chloride, thionyl chloride, POCl$_3$, pivaloyl chloride, and benzyl chloroformate. In an embodiment of the present invention, the activating agent is selected from oxalyl chloride, thionyl chloride, and POCl$_3$. In an embodiment of the present invention, the activating agent is oxalyl chloride.

In an embodiment of the present invention, the weak base is an organic or an inorganic base. In an embodiment of the present invention, the weak base is selected from triethylamine, diisopropylethylamine, tributylamine, dicyclohexylmethylamine, N,N-dimethylaniline, diazabicyclononane, 1,2,2,6,6-pentamethylpiperidine, diisopropylamine, 1,8-diazabicyclo[5.4.0]undec-7-ene, tetramethylguanidine, pyridine, 2,6-lutidine, N-methylmorpholine, and N,N,N',N'-tetramethylethylene diamine. In an embodiment of the present invention, the weak base is selected from KHCO$_3$, NaHCO$_3$, Cs$_2$CO$_3$, K(CO$_3$)$_2$, Na(CO$_3$)$_2$, NaOH, KOH, and a phosphate base. In an embodiment of the present invention, the weak base is triethylamine, diisopropylethylamine, tributylamine, or dicyclohexylmethylamine. In an embodiment of the present invention, the weak base is triethylamine. In an embodiment of the present invention, the weak base is potassium carbonate.

In an embodiment of the present invention, the step of contacting the compound of the formula II with an activating agent to form an acid chloride is conducted in an organic solvent. In an embodiment of the present invention, the step of contacting the compound of the formula II with an activating agent to form an acid chloride is conducted in an organic solvent selected from: dichloromethane, isopropyl acetate, acetonitrile, ethyl acetate, tetrahydrofuran, methyltetrahydrofuran, toluene, methyl acetate, and methyl tert-butyl ether. In an embodiment of the present invention, the step of contacting the compound of the formula II with an activating agent to form an acid chloride is conducted in dichloromethane or isopropyl acetate.

In an embodiment of the present invention, the step of contacting the compound of the formula II with an activating agent to form an acid chloride is conducted in an amide solvent. An amide solvent is an organic solvent containing an amide functionality.

In an embodiment of the present invention, the process is conducted in an amide solvent. In an embodiment of the present invention, the step of contacting the compound of the formula II with an activating agent to form an acid chloride is conducted in an amide solvent. An amide solvent is an organic solvent containing an amide functionality.

In an embodiment of the present invention, the amide solvent is selected from the group consisting of: formamide, N-methylformamide, N,N-dimethylformamide, acetamide, N-methylacetamide, N,N-dimethylacetamide, N,N,N',N'-tetramethylurea, 2-pyrrolidone, and N-methylpyrrolidone. In an embodiment of the present invention, the amide solvent is N,N-dimethylformamide, N,N-dimethylacetamide or N-methylpyrrolidone. In an embodiment of the present invention, the amide solvent is N,N-dimethylformamide.

In an embodiment of the present invention, the process is conducted at a temperature below 50° C. In an embodiment of the present invention, the process is conducted at a temperature below 25° C. In an embodiment of the present invention, the process is conducted at a temperature below 10° C. In an embodiment of the present invention, the process is conducted at a temperature between about 5° C. and 10° C.

The present invention is further directed to a process for preparing a compound of the formula rac-III:

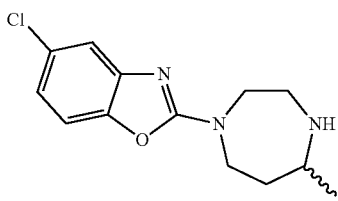

rac-III or a salt thereof,
which comprises:
contacting a compound of the formula IV:

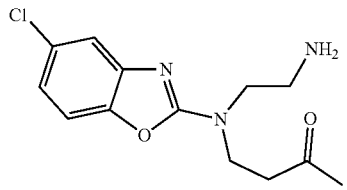

IV with an reducing agent in the presence of a weak base,
to give the compound of the formula rac-III, or a salt thereof.

In an embodiment of the present invention, the reducing agent is selected from sodium triacetoxy borahydride, borahydrides derived from NaBH4 and an N-protected proline, NaBH3CN, NaBH4, LiBH4, DIBAL, and LiAlH4. In an embodiment of the present invention, the reducing agent is sodium triacetoxy borahydride.

In an embodiment of the present invention, the weak base is an organic or an inorganic base. In an embodiment of the present invention, the weak base is selected from triethylamine, diisopropylethylamine, tributylamine, dicyclohexylmethylamine, N,N-dimethylaniline, diazabicyclononane, 1,2,2,6,6-pentamethylpiperidine, diisopropylamine, 1,8-diazabicyclo[5.4.0]undec-7-ene, tetramethylguanidine, pyridine, 2,6-lutidine, N-methylmorpholine, and N,N,N',N'-tetramethylethylene diamine. In an embodiment of the present invention, the weak base is selected from sodium acetate, KHCO3, NaHCO3, Cs2CO3, K(CO3)2, Na(CO3)2, NaOH, KOH, and a phosphate base. In an embodiment of the present invention, the weak base is triethylamine, diisopropylethylamine, tributylamine, or dicyclohexylmethylamine. In an embodiment of the present invention, the weak base is triethylamine. In an embodiment of the present invention, the weak base is potassium carbonate. In an embodiment of the present invention, the weak base is sodium acetate.

In an embodiment of the present invention, the step of contacting a compound of the formula IV with a reducing agent in the presence of a weak base is conducted in an organic solvent. In an embodiment of the present invention, the step of contacting a compound of the formula IV with a reducing agent in the presence of a weak base is conducted in an organic solvent selected from dichloromethane, acetonitrile, toluene, anisole, 1,2-dichloroethane, trifluorotoluene, chlorobenzene, 4-chlorotoluene, isopropyl acetate, ethyl acetate, 2-methyl-2-butanol, ethanol, isopropanol, benzyl alcohol, 1-octanol, tetrahydrofuran, 2-methyltetrahydrofuran, isopropylmethyl ketone, tetramethylurea, N,N-dimethylacetamide, N-ethylpyrrolidinone, triethylamine, dimethyl sulfoxide, cyclopentylmethyl ether, or mixtures thereof. In an embodiment of the present invention, the step of contacting a compound of the formula IV with a reducing agent in the presence of a weak base is conducted in an organic solvent selected from dichloromethane, acetonitrile, toluene, anisole, 1,2-dichloroethane, trifluorotoluene, chlorobenzene, 4-chlorotoluene, isopropyl acetate, ethyl acetate, 2-methyl-2-butanol, or mixtures thereof. In an embodiment of the present invention, the step of contacting a compound of the formula IV with a reducing agent in the presence of a weak base is conducted in dichloromethane.

In an embodiment of the present invention, the step of contacting a compound of the formula IV with a reducing agent in the presence of a weak base is conducted at a temperature between about −40° C. and 40° C. In an embodiment of the present invention, the step of contacting a compound of the formula IV with a reducing agent in the presence of a weak base is conducted at a temperature between about 15° C. and 20° C.

The present invention is further directed to a process for preparing a compound of the formula III:

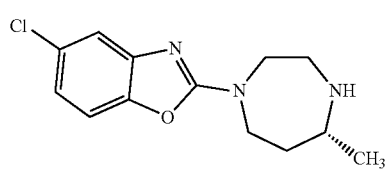

III or a salt thereof,
which comprises:
contacting a compound of the formula IV:

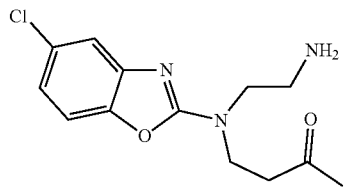

IV with an asymmetric reducing agent in the presence of a weak base, and a terminal reductant to give the compound of the formula III, or a salt thereof.

In an embodiment of the present invention, the asymmetric reducing agent is selected from Ir, Rh, Ru, or Pd with a bidentate phosphine ligand. In an embodiment of the present invention, the asymmetric reducing agent is selected from Ir with difluorophos. In an embodiment of the present invention, the asymmetric reducing agent is selected from Ir or Ru with a diamine ligand of the formula Ar-sulfonyl-1,2-diphenylethylenediamine or Ar-sulfonyl-1,2-trans-diaminocyclohexane where Ar is an aryl group, and with an ancillary ligand selected from p-cymene, benzene, mesitylene, pentamethylcyclopentadienyl, and hexamethylbenzene. In an embodiment of the present invention, the asymmetric reducing agent is selected from Ru with a diamine ligand of the formula Ar-sulfonyl-1,2-diphenylethylenediamine or Ar-sulfonyl-1,2-trans-diaminocyclohexane where Ar is 2,4,6-triisopropylphenyl, and with the ancillary ligand p-cymene. In an embodiment of the present invention, the asymmetric reducing agent is selected from Ir or Rh with a diamine ligand of the formula Ar-sulfonyl-1,2-diphenylethylenediamine or Ar-sulfonyl-1,2-trans-diaminocyclohexane where Ar is an aryl group, and with the ancillary ligand pentamethylcyclopentadienyl. In an embodiment of the present invention, the asymmetric reducing agent is Ir with a diamine ligand of the formula Ar-sulfonyl-1,2-diphenylethylenediamine or Ar-sulfonyl-1,2-trans-diaminocyclohexane where Ar is 2,4,6-triisopropylphenyl, and with the ancillary ligand pentamethylcyclopentadienyl. In an embodiment of the present invention, the asymmetric reducing agent is Rh with a diamine ligand of the formula Ar-sulfonyl-1,2-diphenylethylenediamine or Ar-sulfonyl-1,2-trans-diaminocyclohexane where Ar is 2,4,6-triisopropylphenyl, and with the ancillary ligand pentamethylcyclopentadienyl. In an embodiment of the present invention, the asymmetric reducing agent is a chirally modified borohydride reagent.

In an embodiment of the present invention, the weak base is an organic or an inorganic base. In an embodiment of the present invention, the weak base is selected from triethylamine, diisopropylethylamine, tributylamine, dicyclohexylmethylamine, N,N-dimethylaniline, diazabicyclononane, 1,2,2,6,6-pentamethylpiperidine, diisopropylamine, 1,8-diazabicyclo[5.4.0]undec-7-ene, tetramethylguanidine, pyridine, 2,6-lutidine, N-methylmorpholine, and N,N,N',N'-tetramethylethylene diamine. In an embodiment of the present invention, the weak base is triethylamine, diisopropylethylamine, tributylamine, or dicyclohexylmethylamine. In an embodiment of the present invention, the weak base is triethylamine.

In an embodiment of the present invention, the terminal reductant is selected from formic acid, an alcohol, hydrogen, and a metal hydride. In an embodiment of the present invention, the terminal reductant is formic acid.

In an embodiment of the present invention, the step of contacting a compound of the formula IV with an asymmetric reducing agent in the presence of a weak base is conducted in an organic solvent. In an embodiment of the present invention, the step of contacting a compound of the formula IV with an asymmetric reducing agent in the presence of a weak base is conducted in an organic solvent selected from dichloromethane, acetonitrile, toluene, anisole, 1,2-dichloroethane, trifluorotoluene, chlorobenzene, 4-chlorotoluene, isopropyl acetate, ethyl acetate, 2-methyl-2-butanol, ethanol, isopropanol, benzyl alcohol, 1-octanol, tetrahydrofuran, 2-methyltetrahydrofuran, isopropylmethyl ketone, tetramethylurea, N,N-dimethylacetamide, N-ethylpyrrolidinone, triethylamine, dimethyl sulfoxide, cyclopentylmethyl ether, or mixtures thereof. In an embodiment of the present invention, the step of contacting a compound of the formula IV with an asymmetric reducing agent in the presence of a weak base is conducted in an organic solvent selected from dichloromethane, acetonitrile, toluene, anisole, 1,2-dichloroethane, trifluorotoluene, chlorobenzene, 4-chlorotoluene, isopropyl acetate, ethyl acetate, 2-methyl-2-butanol, or mixtures thereof. In an embodiment of the present invention, the step of contacting a compound of the formula IV with an asymmetric reducing agent in the presence of a weak base is conducted in a mixture of acetonitrile:toluene.

In an embodiment of the present invention, the step of contacting a compound of the formula IV with a reducing agent in the presence of a weak base is conducted at a temperature between about −10 and 20° C. In an embodiment of the present invention, the step of contacting a compound of the formula IV with a reducing agent in the presence of a weak base is conducted at a temperature between about −5 and 5° C. In an embodiment of the present invention, the step of contacting a compound of the formula IV with a reducing agent in the presence of a weak base is conducted at a temperature about 0° C.

In an embodiment of the present invention, the step of contacting a compound of the formula IV with a reducing agent in the presence of a weak base is conducted under a static inert atmosphere. In an embodiment of the present invention, the step of contacting a compound of the formula IV with a reducing agent in the presence of a weak base is conducted with a continuously purged inert atmosphere.

In an alternate embodiment, the present invention is directed to a product prepared by any of the processes disclosed herein.

In an alternate embodiment, the present invention is directed to a compound which is:

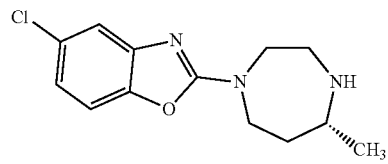 [SMILES: C[C@@H]1CCN(c2nc3cc(Cl)ccc3o2)CCN1]

or a salt thereof.

Within this alternate embodiment, the present invention is directed to a compound which is:

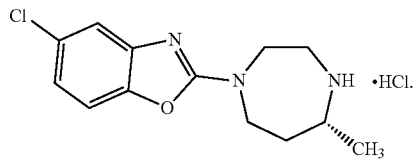 [SMILES: C[C@@H]1CCN(c2nc3cc(Cl)ccc3o2)CCN1]

Within this alternate embodiment, the present invention is directed to a compound which is:

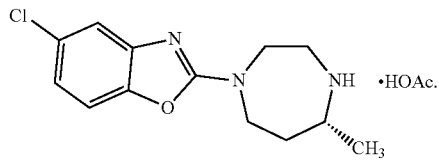 [SMILES: C[C@@H]1CCN(c2nc3cc(Cl)ccc3o2)CCN1]

Within this alternate embodiment, the present invention is directed to a compound which is:

dibenzoyl-D-tartaric acid salt

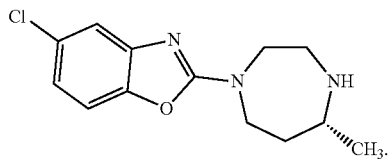

In an alternate embodiment, the present invention is directed to a compound which is:

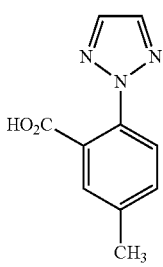

or a salt thereof.

Within this alternate embodiment, the present invention is directed to a compound which is:

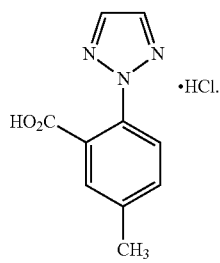

In an alternate embodiment, the present invention is directed to a crystalline form of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone.

In an alternate embodiment, the present invention is directed to an isolated crystalline form of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone.

In an alternate embodiment, the present invention is directed to an anhydrous crystalline form of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone.

In an alternate embodiment, the present invention is directed to [(7R)-4-(5-chloro-1,3-benzoxazol-2-yl)-7-methyl-1,4-diazepan-1-yl][5-methyl-2-(2H-1,2,3-triazol-2-yl)phenyl]-methanone isolated in a form which contains at least about 40 wt. % of the crystalline form. In an alternate embodiment, the present invention is directed to [(7R)-4-(5-chloro-1,3-benzoxazol-2-yl)-7-methyl-1,4-diazepan-1-yl][5-methyl-2-(2H-1,2,3-triazol-2-yl)phenyl]-methanone isolated in a form which contains at least about 50 wt. % of the crystalline form. In an alternate embodiment, the present invention is directed to [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 60 wt. % of the crystalline form. In an alternate embodiment, the present invention is directed to [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 70 wt. % of the crystalline form. In an alternate embodiment, the present invention is directed to [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 80 wt. % of the crystalline form. In an alternate embodiment, the present invention is directed to [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 90 wt. % of the crystalline form. In an alternate embodiment, the present invention is directed to [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 95 wt. % of the crystalline form. In an alternate embodiment, the present invention is directed to [(7R)-4-(5-chloro-1,3-benzoxazol-2-yl)-7-methyl-1,4-diazepan-1-yl][5-methyl-2-(2H-1,2,3-triazol-2-yl)phenyl]-methanone isolated in a form which contains at least about 98 wt. % of the crystalline form. In an alternate embodiment, the present invention is directed to [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 99 wt. % of the crystalline form.

In an alternate embodiment, the present invention is directed to an anhydrous form of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone.

In an alternate embodiment, the present invention is directed to the crystalline form I of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone.

In an alternate embodiment, the present invention is directed to form I of [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 50 wt. % of form I. In an alternate embodiment, the present invention is directed to form I of [(7R)-4-(5-chloro-1,3-benzoxazol-2-yl)-7-methyl-1,4-diazepan-1-yl][5-methyl-2-(2H-1,2,3-triazol-2-yl)phenyl]-methanone isolated in a form which contains at least about 60 wt. % of form I. In an alternate embodiment, the present invention is directed to form I of [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 70 wt. % of form I. In an alternate embodiment, the present invention is directed to form I of [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 80 wt. % of form I. In an alternate embodiment, the present invention is directed to form I of [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 90 wt. % of form I. In an alternate embodiment, the present invention is directed to form I of [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 95 wt. % of form I. In an alternate embodiment, the present invention is directed to form I of [(7R)-4-(5-chloro-1,3-benzoxazol-2-yl)-7-methyl-1,4-diazepan-1-yl][5-methyl-2-(2H-1,2,3-triazol-2-yl)phenyl]-methanone isolated in a form which contains at least about 98 wt. % of form I. In an alternate embodiment, the present invention is directed to form I of [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 99 wt. % of form I.

In an alternate embodiment, the present invention is directed to the crystalline form II of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone.

In an alternate embodiment, the present invention is directed to form II of [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 50 wt. % of form II. In an alternate embodiment, the present invention is directed to form II of [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 60 wt. % of form II. In an alternate embodiment, the present invention is directed to form II of [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 70 wt. % of form II. In an alternate embodiment, the present invention is directed to form II of [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 80 wt. % of form II. In an alternate embodiment, the present invention is directed to form II of [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 90 wt. % of form II. In an alternate embodiment, the present invention is directed to form II of [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 95 wt. % of form II. In an alternate embodiment, the present invention is directed to form II of [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 98 wt. % of form II. In an alternate embodiment, the present invention is directed to form II of [(7R)-4-(5-chloro-1,3-benzoxazol-2-yl)-7-methyl-1,4-diazepan-1-yl][5-methyl-2-(2H-1,2,3-triazol-2-yl)phenyl]methanone isolated in a form which contains at least about 99 wt. % of form II.

Anhydrous form I of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone is prepared by crystallization of a sample of [(7R)-4-(5-chloro-1,3-benzoxazol-2-yl)-7-methyl-1,4-diazepan-1-yl][5-methyl-2-(2H-1,2,3-triazol-2-yl)phenyl]methanone from various organic solvents, including a mixture of isopropyl acetate/heptane. Anhydrous form I of the compound [(R)-4-(5-chloro-benzooxazol-2-yl)-7-methyl-[1,4]diazepan-1-yl]-(5-methyl-2-[1,2,3]triazol-2-yl-phenyl)methanone is prepared by crystallization of a sample of [(7R)-4-(5-chloro-1,3-benzoxazol-2-yl)-7-methyl-1,4-diazepan-1-yl][5-methyl-2-(2H-1,2,3-triazol-2-yl)phenyl]methanone at a temperature less than about 35° C. An embodiment of the present invention is directed to a process for the preparation of anhydrous form I of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone which comprises crystallization of [(7R)-4-(5-chloro-1,3-benzoxazol-2-yl)-7-methyl-1,4-diazepan-1-yl][5-methyl-2-(2H-1,2,3-triazol-2-yl)phenyl]methanone from a mixture of isopropyl acetate/heptane at a temperature less than about 35° C.

Anhydrous form II of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone is prepared by crystallization of a sample of [(7R)-4-(5-chloro-1,3-benzoxazol-2-yl)-7-methyl-1,4-diazepan-1-yl][5-methyl-2-(2H-1,2,3-triazol-2-yl)phenyl]methanone from various organic solvents, including a mixture of isopropyl acetate/heptane. Anhydrous form II of the compound [(R)-4-(5-chloro-benzooxazol-2-yl)-7-methyl-[1,4]diazepan-1-yl]-(5-methyl-2-[1,2,3]triazol-2-yl-phenyl)methanone is prepared by crystallization of a sample of [(7R)-4-(5-chloro-1,3-benzoxazol-2-yl)-7-methyl-1,4-diazepan-1-yl][5-methyl-2-(2H-1,2,3-triazol-2-yl)phenyl]methanone at a temperature greater than about 40° C. An embodiment of the present invention is directed to a process for the preparation of anhydrous form II of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone which comprises crystallization of [(7R)-4-(5-chloro-1,3-benzoxazol-2-yl)-7-methyl-1,4-diazepan-1-yl][5-methyl-2-(2H-1,2,3-triazol-2-yl)phenyl]-methanone from a mixture of isopropyl acetate/heptane at a temperature greater than about 40° C. An embodiment of the present invention is directed to a process for the preparation of anhydrous form II of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone which comprises crystallization of [(7R)-4-(5-chloro-1,3-benzoxazol-2-yl)-7-methyl-1,4-diazepan-1-yl][5-methyl-2-(2H-1,2,3-triazol-2-yl)phenyl]methanone from a mixture of isopropyl acetate/heptane by sonication seeding at a temperature greater than about 40° C.

Anhydrous form I and Anhydrous form II are enatiotropically related. Anhydrous Form I is the most stable crystalline phase at 25° C. Anhydrous form I is the thermodynamically most stable crystalline form at temperatures ≤35° C. The transition temperature between anhydrous form I and anhydrous form II was determined by slurring a mixture containing equal amounts of the two forms in EtOH at various temperatures. The transition temperature between anhydrous form I and anhydrous form II is between 35 and 40° C. Anhydrous form II is the thermodynamically most stable crystalline form at temperatures ≥40° C. Anhydrous Form II can be synthesized using a crystallization process that is more efficient and results in improved particle size and morphology control relative to anhydrous form I. Anhydrous form II has better crystallinity, better filtration properties and gives better purity rejection than anhydrous form I. Anhydrous form II has better processability for preparing formulations than Anhydrous form I.

X-ray powder diffraction studies are widely used to characterize molecular structures, crystallinity, and polymorphism. The X-ray powder diffraction patterns were generated on a Philips Analytical X'Pert PRO X-ray Diffraction System with PW3040/60 console. A PW3373/00 ceramic Cu LEF X-ray tube K-Alpha radiation was used as the source.

In addition to the X-ray powder diffraction patterns described above, anhydrous form I of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone and anhydrous form II of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone were further characterized by solid-state carbon-13 nuclear magnetic resonance (NMR) spectra. The solid-state carbon-13 NMR spectra were obtained on a Bruker DSX 400WB NMR system using a Bruker 4 mm H/X CPMAS probe. The carbon-13 NMR spectra utilized proton/carbon-13 cross-polarization magic-angle spinning with variable-amplitude cross polarization, and TPPM decoupling at 80 kHz. The samples were spun at 10.0 kHz, and a total of 1024 scans were collected with a recycle delay of 5 seconds. A line broadening of 10 Hz was applied to the spectra before FT was performed. Chemical shifts are reported on the TMS scale using the carbonyl carbon of glycine (176.70 p.p.m.) as a secondary reference.

DSC data were acquired using TA Instruments DSC 2910 or equivalent instrumentation. A sample with a weight between 2 and 6 mg was weighed into a pan and the pan was crimped. This pan was placed in the sample position in the calorimeter cell. An empty pan was placed in the reference position. The calorimeter cell was closed and a flow of nitrogen is passed through the cell. The heating program was set to heat the sample at a heating rate of 10° C./min to a temperature of approximately 200° C. When the run was completed, the data were analyzed using the DSC analysis program in the system software. The observed endotherms were integrated between baseline temperature points that are above and below the temperature range over which the endotherm is observed. The data reported are the onset temperature, peak temperature and enthalpy.

FIG. 1 shows an X-ray powder diffraction pattern of anhydrous form I of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone. The anhydrous form I of the compound [(7R)-4-(5-chloro-1,3-benzoxazol-2-yl)-7-methyl-1,4-diazepan-1-yl][5-methyl-2-(2H-1,2,3-triazol-2-yl)phenyl]-methanone is characterized by diffraction peaks corresponding to d-spacings of 8.46, 6.27, 5.53 and 3.45 angstroms.

Peak Position, d-Spacing and Peak Height for FIG. 1.

| Pos. [°2Th.] | d-spacing [Å] | Height [cts] |
|---|---|---|
| 2.1947 | 40.25602 | 881.32 |
| 3.3561 | 26.32653 | 189.15 |
| 6.9524 | 12.71464 | 45.18 |
| 10.4603 | 8.45726 | 158.26 |
| 14.1262 | 6.26971 | 591.35 |
| 15.2644 | 5.80466 | 345.10 |
| 16.0273 | 5.53004 | 736.18 |
| 17.5256 | 5.06051 | 145.24 |
| 21.0662 | 4.21729 | 164.92 |
| 22.4215 | 3.96536 | 26.67 |
| 25.8414 | 3.44780 | 319.11 |

Figure 2:
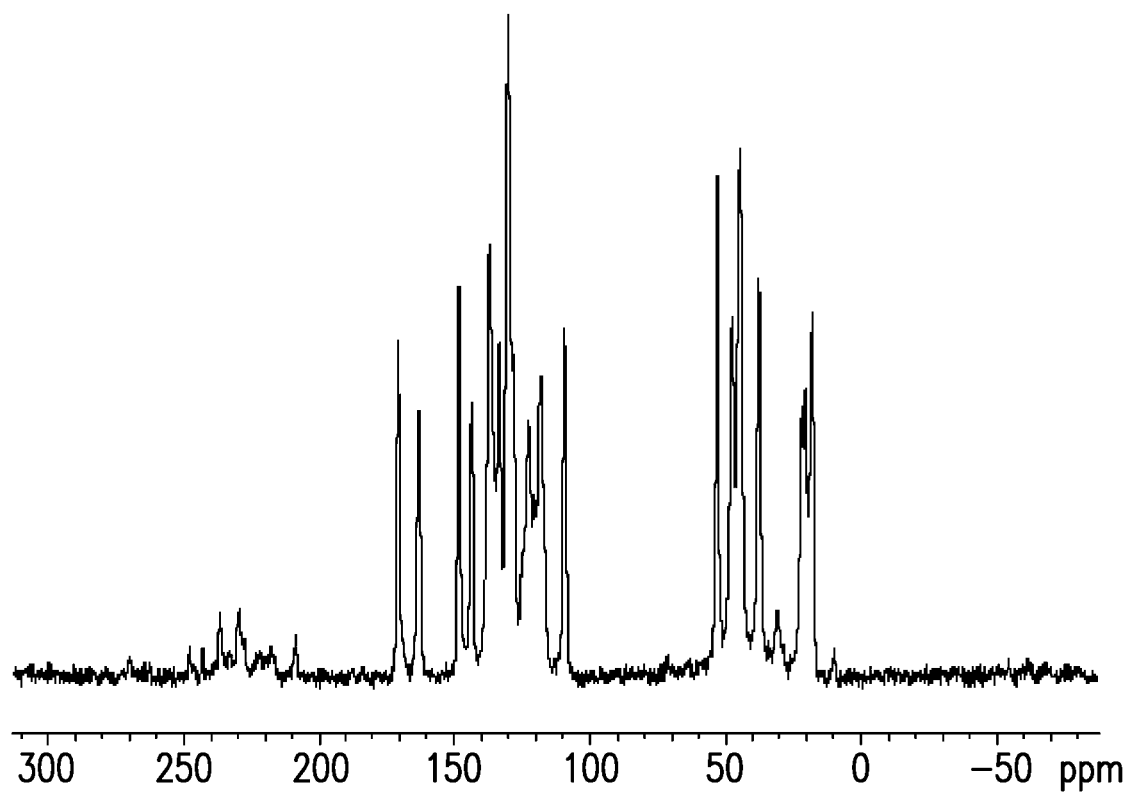
FIG. 2 shows a carbon-13 cross-polarization magic-angle spinning (CPMAS) nuclear magnetic resonance (NMR) spectrum of anhydrous Form I of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone.

FIG. 2 shows a carbon-13 cross-polarization magic-angle spinning (CPMAS) nuclear magnetic resonance (NMR) spectrum of anhydrous form I of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone. The anhydrous form I of the compound [(7R)-4-(5-chloro-1,3-benz-oxazol-2-yl)-7-methyl-1,4-diazepan-1-yl][5-methyl-2-(2H-1,2,3-triazol-2-yl)phenyl]-methanone is characterized by carbon-13 cross-polarization magic-angle spinning (CP-MAS) nuclear magnetic resonance (NMR) peaks corresponding to 130.3, 44.6 and 37.6 p.p.m. The spectrum is further characterized by peaks corresponding to 118.1, 122.6, 143.6 and 21.8 p.p.m.

Chemical Shift and Relative Intensity for FIG. 2

| Peak (ppm) | Relative Intensity |
|---|---|
| 130.3 | 100 |
| 44.6 | 80 |
| 53.0 | 76 |
| 137.0 | 66 |
| 37.6 | 60 |
| 148.3 | 59 |

Chemical Shift and Relative Intensity for FIG. 2

| Peak (ppm) | Relative Intensity |
|---|---|
| 18.0 | 55 |
| 47.7 | 55 |
| 109.4 | 53 |
| 170.8 | 51 |
| 133.5 | 50 |
| 128.6 | 49 |
| 118.1 | 45 |
| 20.4 | 44 |
| 143.6 | 41 |
| 21.8 | 41 |
| 163.1 | 40 |
| 122.6 | 39 |
| 120.4 | 28 |

Figure 3:
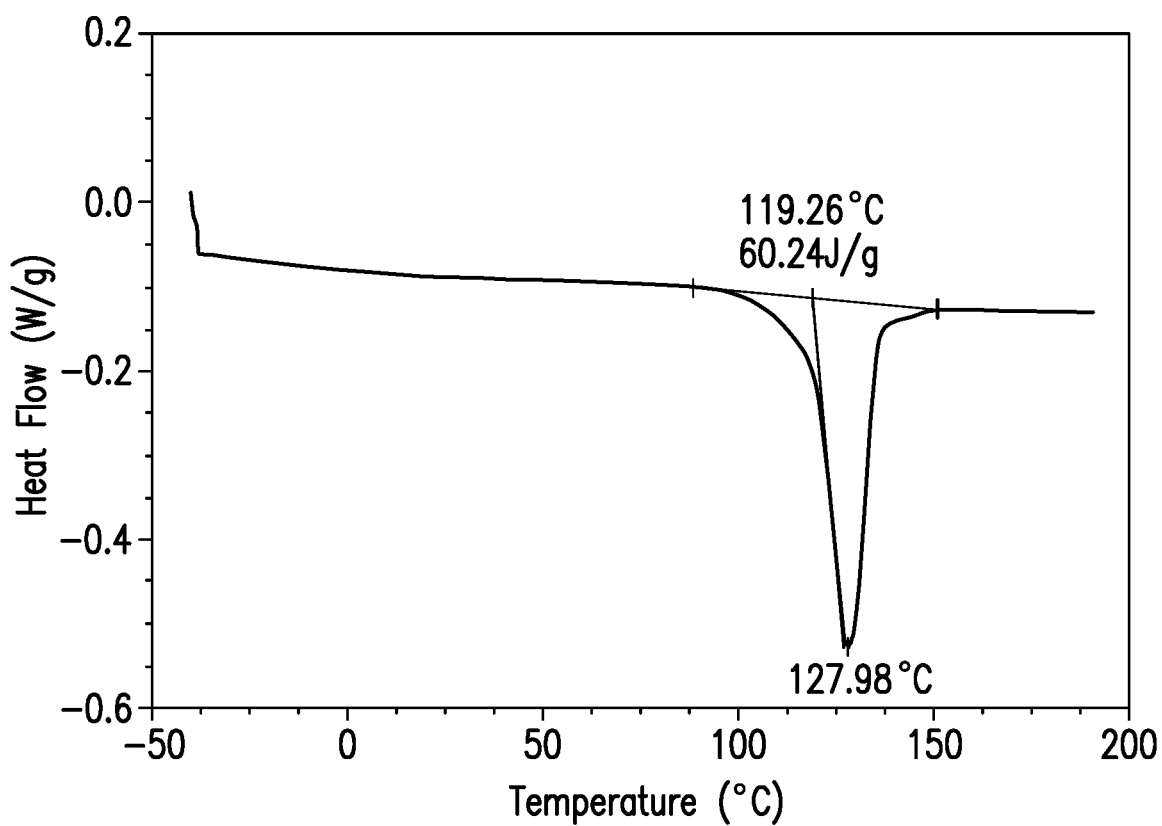
FIG. 3 shows a DSC curve of anhydrous Form I of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone.

FIG. 3 shows a DSC curve of the anhydrous form I of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone. The anhydrous form I of the compound [(7R)-4-(5-chloro-1,3-benzoxazol-2-yl)-7-methyl-1,4-diazepan-1-yl][5-methyl-2-(2H-1,2,3-triazol-2-yl)phenyl]-methanone is characterized by a DSC curve with an endotherm with an extrapolated onset temperature of 119.3° C., a peak temperature of 128.0° C. and enthalpy of 60.2 J/g, associated with the melting of anhydrous form I of the compound [(7R)-4-(5-chloro-1,3-benzoxazol-2-yl)-7-methyl-1,4-diazepan-1-yl][5-methyl-2-(2H-1,2,3-triazol-2-yl)phenyl]-methanone.

Figure 4:
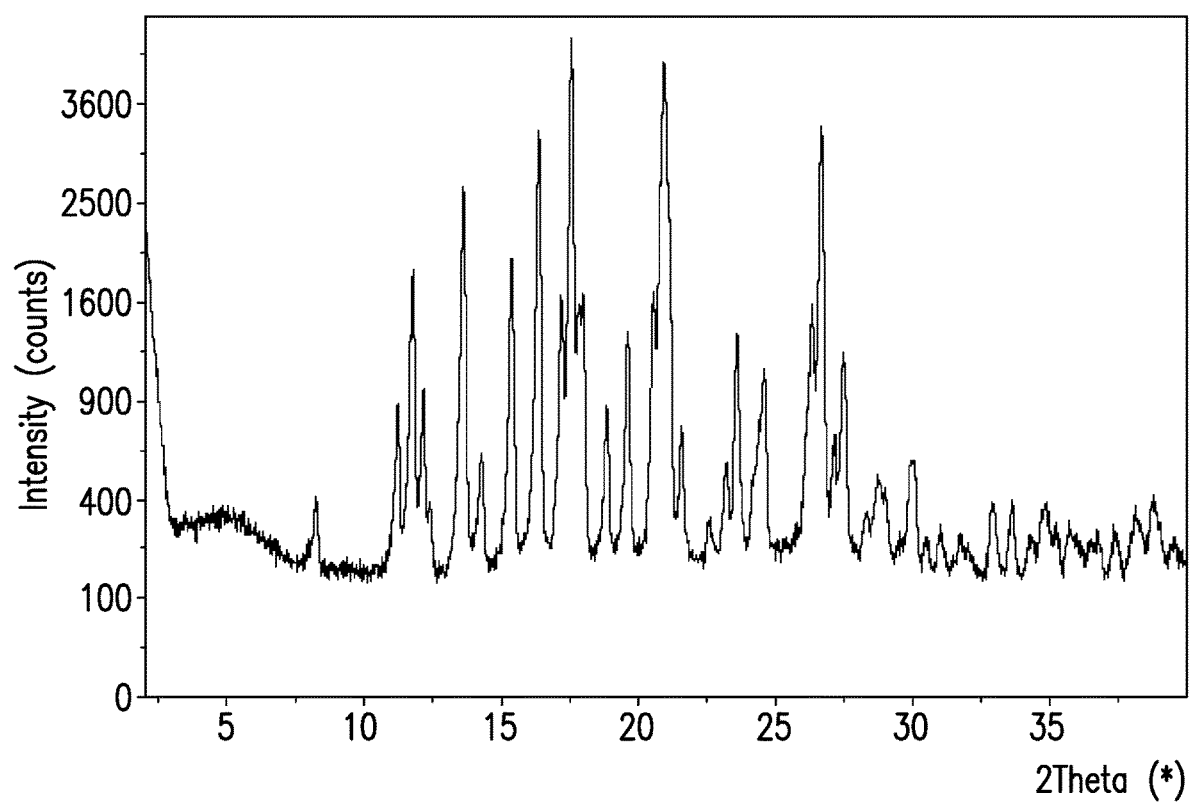
FIG. 4 shows an X-ray diffraction pattern of anhydrous Form II of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone.

FIG. 4 shows an X-ray powder diffraction pattern of form II of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone. The anhydrous form II of the compound[(7R)-4-(5-chloro-1,3-benzoxazol-2-yl)-7-methyl-1,4-diazepan-1-yl][5-methyl-2-(2H-1,2,3-triazol-2-yl)phenyl]-methanone is characterized by diffraction peaks corresponding to d-spacings of 5.04, 4.23 and 3.33 angstroms, further characterized by diffraction peaks corresponding to d-spacings of 6.48, 5.74, and 5.40 angstroms, and further characterized by diffraction peaks corresponding to d-spacings of 7.48, 4.51 and 3.76 angstroms.

Peak Position, d-Spacing and Peak Height for FIG. 4.

| Pos. [°2Th.] | d-spacing [Å] | Height [cts] |
|---|---|---|
| 2.1278 | 41.52031 | 781.03 |
| 11.2716 | 7.85028 | 139.75 |
| 11.8308 | 7.48050 | 319.24 |
| 12.1964 | 7.25703 | 164.00 |
| 13.6736 | 6.47618 | 521.27 |
| 14.3153 | 6.18731 | 82.24 |
| 15.4344 | 5.74112 | 539.17 |
| 16.4169 | 5.39967 | 682.73 |
| 17.2498 | 5.14077 | 370.81 |
| 17.6032 | 5.03836 | 1170.49 |
| 17.9378 | 4.94513 | 440.26 |
| 18.9081 | 4.69349 | 171.73 |
| 19.6779 | 4.51160 | 240.91 |
| 21.0014 | 4.23017 | 1070.68 |
| 21.6376 | 4.10721 | 174.89 |
| 23.6680 | 3.75925 | 300.98 |
| 24.6272 | 3.61497 | 246.43 |
| 26.3743 | 3.37934 | 370.32 |

-continued

Peak Position, d-Spacing and Peak Height for FIG. 4.

| Pos. [°2Th.] | d-spacing [Å] | Height [cts] |
| --- | --- | --- |
| 26.7454 | 3.33328 | 854.82 |
| 27.5276 | 3.24032 | 290.17 |
| 30.0721 | 2.97169 | 125.18 |
| 32.9814 | 2.71591 | 64.81 |
| 33.6808 | 2.66110 | 56.84 |

Figure 5:
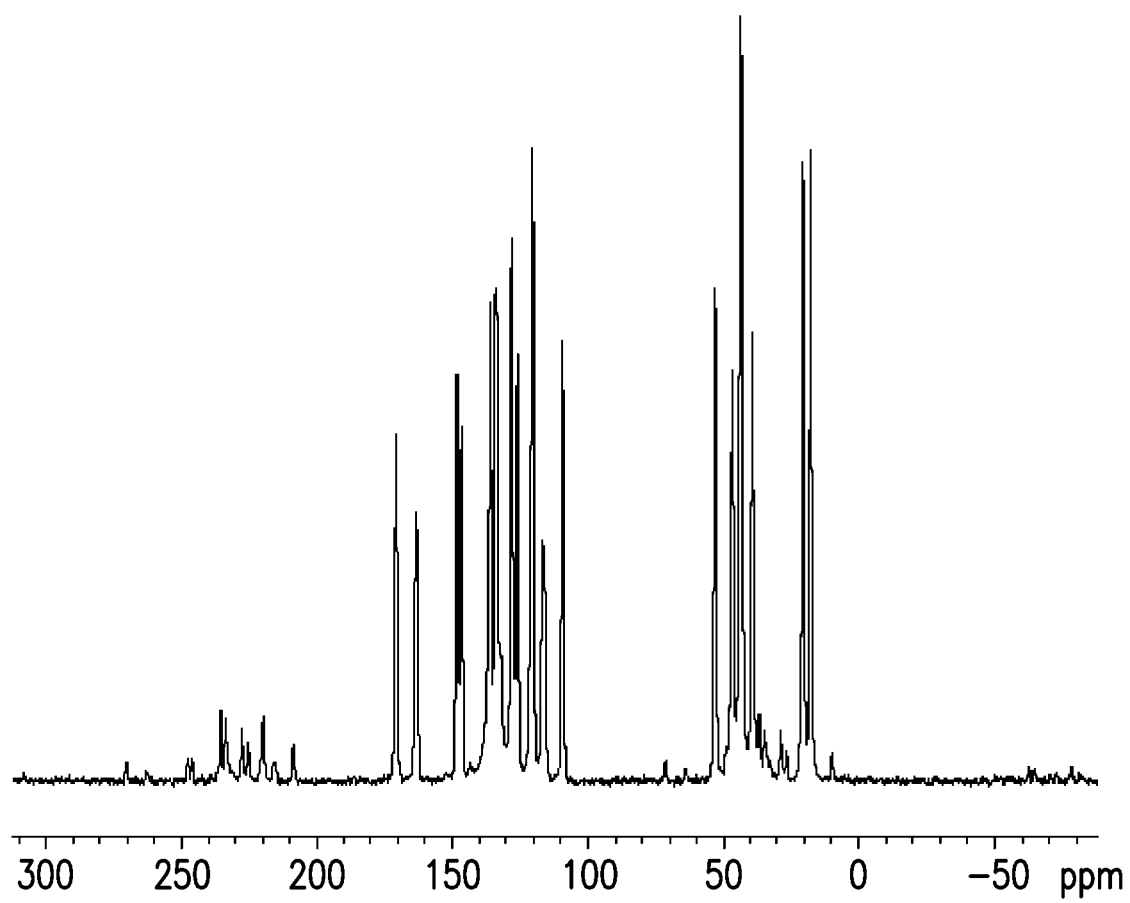
FIG. 5 shows a carbon-13 cross-polarization magic-angle spinning (CPMAS) nuclear magnetic resonance (NMR) spectrum of anhydrous Form II of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone.

FIG. 5 shows a carbon-13 cross-polarization magic-angle spinning (CPMAS) nuclear magnetic resonance (NMR) spectrum of the anhydrous form II of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone. The anhydrous form II of the compound [(7R)-4-(5-chloro-1,3-benzoxazol-2-yl)-7-methyl-1,4-diazepan-1-yl][5-methyl-2-(2H-1,2,3-triazol-2-yl)phenyl]-methanone is characterized by carbon-13 cross-polarization magic-angle spinning (CPMAS) nuclear magnetic resonance (NMR) peaks corresponding to 43.5, 126.0 and 39.3 p.p.m. The spectrum is further characterized by peaks corresponding to 146.7 and 116.7 p.p.m.

Chemical Shift and Relative Intensity for FIG. 5

| Peak (ppm) | Relative Intensity |
| --- | --- |
| 43.5 | 100 |
| 120.4 | 83 |
| 17.9 | 82 |
| 20.6 | 81 |
| 128.2 | 71 |
| 53.1 | 64 |
| 134.2 | 64 |
| 133.7 | 63 |
| 136.0 | 62 |
| 39.3 | 59 |
| 109.3 | 58 |
| 126.0 | 56 |
| 46.7 | 54 |
| 148.3 | 53 |
| 146.7 | 46 |
| 170.8 | 45 |
| 163.3 | 35 |
| 116.7 | 32 |

Figure 6:
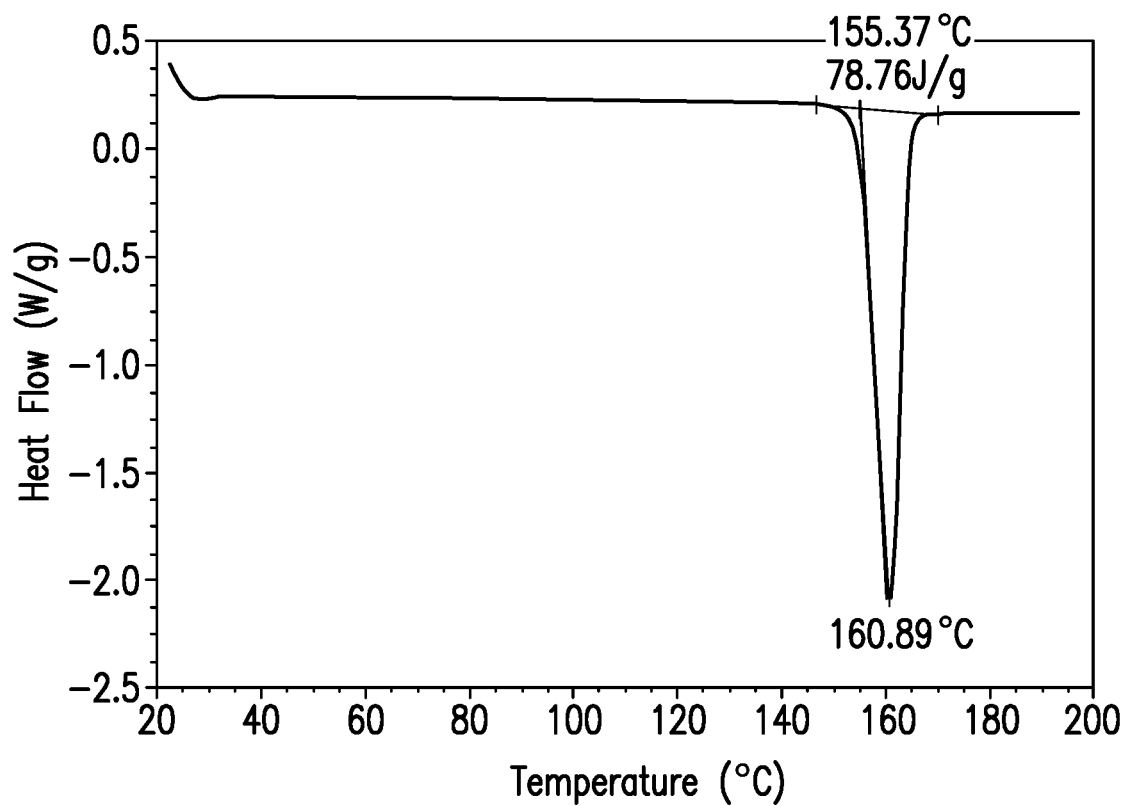
FIG. 6 shows a DSC curve of anhydrous Form II of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone.

FIG. 6 shows a DSC curve of the anhydrous form II of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone. The anhydrous form I of the compound [(7R)-4-(5-chloro-1,3-benzoxazol-2-yl)-7-methyl-1,4-diazepan-1-yl][5-methyl-2-(2H-1,2,3-triazol-2-yl)phenyl]-methasone is characterized by a DSC curve with an extrapolated onset temperature of 155.4° C., a peak temperature of 160.9° C. and enthalpy of 78.8 J/g, associated with the melting of anhydrous form II of the compound [(7R)-4-(5-chloro-1,3-benzoxazol-2-yl)-7-methyl-1,4-diazepan-1-yl][5-methyl-2-(2H-1,2,3-triazol-2-yl)phenyl]methanone.

The subject compound of the formula I is disclosed as an antagonist of orexin receptors in US Patent Application Publication US 2008/0132490, PCT Patent Publication WO 2008/069997, and Cox et al., J. Med. Chem. 2010, 53, 5320-5332. This compounds is disclosed as having activity in antagonizing the human orexin-1 (OX1) receptor with a Ki of 0.55 nM and in antagonizing the human orexin-2 (OX2) receptor with a Ki of 0.35 nM. The processes disclosed in US 2008/0132490, WO 2008/069997 and Cox et al., J. Med. Chem. 2010, 53, 5320-5332 is lengthy, suffers from low yields, necessitates multiple protecting groups, relies on chiral chromatography to prepare a single isomer and requires microwave technology to prepare the acid intermediate. Relative to the processes disclosed in US 2008/0132490 and WO 2008/069997, the present invention provides an improved process for the efficient, scalable, chromatography-free and cost-effective preparation of the formula I in five steps, to give higher isolated yield of the subject compound. The processes of the present invention increase the efficiency of the synthetic route to the desired product by reducing the number steps and allowing access to a single enantiomer without recourse to chromatography. In addition, use of protecting groups are minimized, low yielding steps are circumvented, and an asymmetric reduction using either metal catalysis is employed to establish the chiral center.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the compound with the designation of specific stereochemistry. When the compounds of the present invention contain one chiral center, the term "stereoisomer" includes both enantiomers and mixtures of enantiomers, such as the specific 50:50 mixture referred to as a racemic mixtures.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$ alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to final compounds of Formula I are meant to also include the pharmaceutically acceptable salts.

The term "salts" refers to salts prepared from acceptable bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from organic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids.

Exemplifying the invention is the use of the compounds disclosed in the Examples and herein. Specific compounds within the present invention include a compound which selected from the group consisting of the compounds disclosed in the following Examples and salts thereof and individual enantiomers or diastereomers thereof.

The subject compound of Formula I is useful in a method of antagonizing orexin receptor activity in a patient such as a mammal in need of such inhibition comprising the administration of an effective amount of the compound. The present invention is directed to the use of the compounds disclosed herein as antagonists of orexin receptor activity. In addition to primates, especially humans, a variety of other mammals can be treated according to the method of the present invention. The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for antagonizing orexin receptor activity or treating the disorders and diseases noted herein in humans and animals.

The subject treated in the present methods is generally a mammal, such as a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The orexin receptors have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with orexin receptors, including one or more of the following conditions or diseases: sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders including overeating and bulimia nervosa, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, addictive feeding, dependence or withdrawal from substances including alcohol, amphetamines, cannabis, cocaine, hallucinogens, inhalants, nicotine, opioids, phencyclidine, sedatives, hypnotics or anxiolytics); movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); attention deficit/hyperactivity disorder (ADHD); conduct disorder; migraine (including migraine headache); urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in specific embodiments the present invention provides methods for: enhancing the quality of sleep; augmenting sleep maintenance; increasing REM sleep; increasing stage 2 sleep; decreasing fragmentation of sleep patterns; treating insomnia; enhancing cognition; increasing memory retention; treating or controlling obesity; treating or controlling depression; treating, controlling, ameliorating or reducing the risk of epilepsy, including absence epilepsy; treating or controlling pain, including neuropathic pain; treating or controlling Parkinson's disease; treating or controlling psychosis; or treating, controlling, ameliorating or reducing the risk of schizophrenia, in a mammalian patient in need thereof which comprises administering to the patient a therapeutically effective amount of a compound of the present invention.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of orexin receptors. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, include, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor a agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA: cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579 by Glaxo; (g) PPARδ agonists; (h) PPAR α/δ agonists, such as muraglitazar, and the compounds disclosed in U.S. Pat. No. 6,414,002; and (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255; (2) protein tyrosine phosphatase-1B (PTP-1B) inhibitors; (3) cannabinoid receptor ligands, such as cannabinoid CB$_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate; (7) neuropeptide Y1 antagonists, such as BIBP3226, J-115814, BIBO 3304, LY-357897, CP-671906, GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) other Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065; (18) galanin antagonists; (19) CCK agonists; (20) CCK-A (cholecystokinin-A) agonists, such as AR-R 15849, GI 181771, JMV-180, A-71378, A-71623 and SR14613; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (13-HSD-1); 26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6,beta-Ala11,Phe13,Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (GlaxoSmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, MK-431, P93/01, TSL 225, TMC-2A/2B/2C, FE 999011, P9310/K364, VIP 0177, SDZ 274-444; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIBO 3304, LY-357897, CP-671906, GI-264879A; (56) Opioid antagonists such as nalmefene (Revex ®), 3-methoxynaltrexone, naloxone, naltrexone; (57) 11β HSD-1 (11-beta hydroxy steroid dehydrogenase type 1) inhibitor such as BVT 3498, BVT 2733; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H3 antagonists; AMPA agonists; PDE IV inhibitors; $GABA_A$ inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the subject compound may be employed in combination with an anoretic agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptble salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: 2-MeTHF: 2-methyltetrahydrofuran; Ac: acetyl; Ar: aryl; AY: assay yield; Bn: benzyl; Boc: tert-butyloxy carbonyl; Boc$_2$O: di-tert-butyldicarbonate; BSA: bovine serum albumin; Cbz: carbobenzyloxy; CDI: carbonyl diimidazole; CSA: camphor sulfonic acid; DEAD: diethylazodicarboxylate; DCE: dichloroethane; DCM: dichloromethane; DIPEA: N,N-diisopropylethylamine; DMF: N,N-dimethylformamide; DMSO: dimethylsulfoxide; EDC: N-(3-dimethylaminopropyl)-N'-ethylcarbodiimide; Et: ethyl; EtOH: ethanol; Et$_3$N: triethylamine; GC-FID: gas chromatography-flame ionization detector; HOBT: hydroxybenzotriazole hydrate; HPLC: high performance liquid chromatography; LC-MS: liquid chromatography-mass spectrometry; LRMS: low resolution mass spectrometry; Me: methyl; MTBE: methyl tert-butyl ether; NAD: nicotinamide adenine dinucleotide; NMP: N-methylpyrrolidone; PdCl$_2$(dppf)-CH$_2$Cl$_2$: [1,1'-Bis(diphenylphosphino)ferrocene] dichloropalladium(II) dichloromethane; Ph: phenyl; PhMe: toluene; PLP: pyridoxal-5' phosphate; rt: room temperature; SOCl$_2$: thionyl chloride; T$_3$P: 1-propylphosphonic anhydride; t-Bu: tert-butyl; TsCl: tosyl chloride; TFA: trifluoracetic acid; THF: tetrahydrofuran. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes and examples may be varied to facilitate the reaction or to avoid unwanted reaction products. The following examples are provided so that the invention might be more fully understood. These examples are illustrative only and should not be construed as limiting the invention in any way.

Example 1

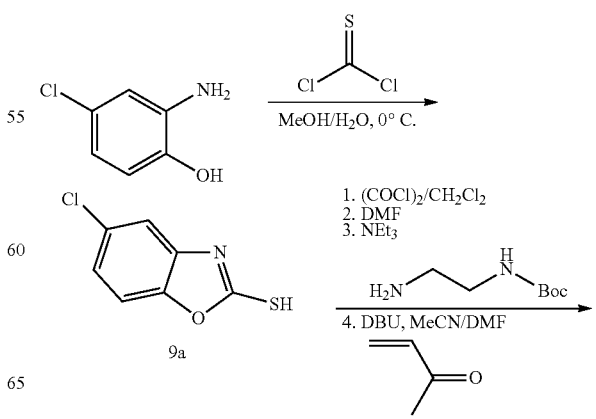

-continued

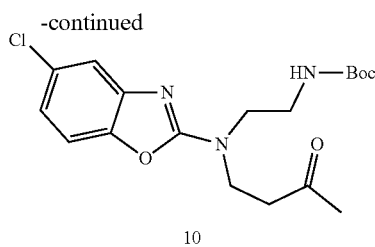

10

5-Chloro-1,3-benzoxazole-2-thiol (9a)

2-Amino-4-chlorophenol (2.50 kg, 17.4 mol) was charged to a vessel and suspended in water (52 L) and methanol (10.4 L). High dilution was required to prevent slow and difficult filtration of the product. The mixture was stirred, cooled to 0° C., then thiophosgene (2.00 kg, 17.4 mol) was added to the suspension ensuring that the internal temperature remained at 5° C. throughout the addition. Water (8 L) and methanol (2 L) were added to aid stirring and the slurry was warmed to 13° C. for 1 h, followed by aging at 20° C. for a further 1 h. The slurry was then filtered and the solid washed with water (5 L). The batch was repeated and combined to dry in a vacuum oven (T=40° C.) for 15 h to give 9a (5.81 kg, 31.3 mol). The data corresponds to the commercially available material. $^1$H NMR (400 MHz, $d_6$-DMSO): δ 7.51 (d, 1H, J=9.2 Hz), 7.30 7.26 (m, 2H). $^{13}$C NMR (100.6 MHz, $d_6$-DMSO): δ 181.2, 147.4, 133.1, 129.7, 123.9, 111.6, 110.8. HRMS (ESI): m/z [M$^+$+H] calcd for $C_7H_4ClNOS$: 185.9780; found: 185.9785.

{2-[(5-Chloro-benzooxazol-2-yl)-(3-oxo-butyl)-amino]-ethyl}-carbamic acid tert-butyl ester (10)

Thiol 9a (10.5 kg, 54.6 mol) was added to a vessel and suspended in DCM (141 kg). Oxalyl chloride (10.4 kg, 82.3 mol) was added (slightly endothermic) followed by DMF (40.0 kg, 547 mol) over 1.25 h, such that the batch temperature was ≤25° C. The batch was aged at 20° C. for approximately 30 min, HPLC analysis showed reaction to be complete. The batch was cooled to 10° C. then triethylamine (16.64 kg, 164.4 mol) was added via a sub-surface sample line at such a rate as to maintain a batch temperature of ≤10° C. A sub-surface addition protocol was required to prevent build up of triethylamine hydrochloride solid on the walls of the vessel. The batch was cooled to 0° C., then a solution of N-Boc-ethylenediamine (10.5 kg, 61.2 mol) in DCM (10 kg) was added such that the batch temperature was ≤10° C. The reaction was warmed to 20° C. and stirred for 2.5 h, HPLC analysis showed the reaction to be complete. Water (63.6 kg) was charged to the batch and the mixture stirred for 5 min. The layers were separated and the aqueous phase re-extracted with DCM (42.2 kg). The organic solutions were then combined and approximately half of the total DCM volume was distilled from the batch under vacuum whilst maintaining a temperature of ≤40° C. MeCN (83.3 kg) was then added and the remaining DCM removed by distillation (0.5 mol % DCM left by $^1$H NMR wrt MeCN). MVK (4.61 kg, 65.8 mol) was added to the batch followed by DBU (4.17 kg, 27.4 mol) such that the temperature was ≤20° C. The batch was aged for 10 h at 20° C. then analyzed by HPLC. The reaction was then diluted with water (42.4 kg) and aged for a further 30 min. The mixture was filtered and the slurry washed with MeCN (33.3 kg). The solid was washed with MeCN (~10 L) then dried in a vacuum oven (T=60° C.) for 22 h. MVK adduct 10 (15.5 kg) was isolated as an off-white solid. mp 145-148° C. $^1$H NMR (400 MHz, CDCl$_3$): δ 7.24 (d, 1H, J=2.3 Hz), 7.09 (d, 1H, J=8.5 Hz), 6.91 (dd, 1H, J=8.5, 2.3 Hz), 5.06 (s, 1H, br), 3.73 (t, 2H, J=6.7 Hz), 3.63 (t, 2H, J=6.1 Hz), 3.37 (d, 2H, br), 2.89 (t, 2H, J=6.7 Hz), 2.14 (s, 3H), 1.33 (s, 9H). $^{13}$C NMR (100.6 MHz, CDCl$_3$): δ 206.7, 163.0, 156.0, 147.4, 144.6, 129.2, 120.3, 116.6, 109.2, 79.4, 49.3, 44.3, 41.9, 39.1, 30.2, 28.3. HRMS (ESI): m/z [M$^+$+H] calcd for $C_{18}H_{24}ClN_3O_4$: 382.1534; found: 382.1544.

Example 2

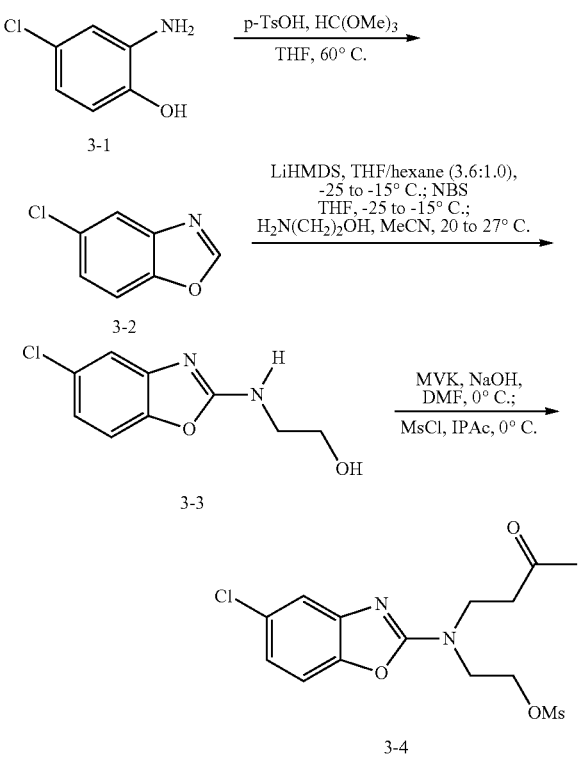

5-Chlorobenzoxazole (3-2)

To a 250 mL 3-neck round bottom flask equipped with a distillation head, glass stopper, septum, thermocouple and magnetic stir bar was charged 2-amino-4-chlorophenol (20.00 g, 0.139 mol). The solid was dissolved in THF (60 mL) and p-TsOH (0.265 g, 1.39 mmol) was added. The brown solution was warmed to 60° C. over 10 min and aged for 90 min. HPLC assay of the reaction mixture showed 1 LCAP unreacted starting material. The temperature was increased from 60° C. to 74° C., and at 63° C. solvent distillation began. A total of 58 mL was collected during the first distillation. The mixture was diluted with THF (60 mL) and a total of 67 mL of solvent was removed between 71 and 84° C. The mixture was again diluted with THF (60 mL) and 61 mL of solvent was removed between 74 and 114° C. The dark brown solution was cooled to room temperature. The final mass of the solution was 27.96 g. Analysis of the crude stream by $^1$H NMR showed 0.1 wt % MeOH present in the sample. $^1$H NMR (500 MHz, CDCl$_3$): δ=8.10 (s, 1H), 7.76 (d, J=1.5 Hz, 1H), 7.50 (d, J=8.7 Hz, 1H), 7.36 ppm (dd, J=8.7, 1.7 Hz, 1H).

2-[(5-Chloro-1,3-benzoxazol-2-yl)amino]ethanol (3-3)

A 500 mL 3-neck round bottom flask equipped with a septum, thermocouple, 125 mL addition funnel, inert gas inlet and magnetic stir bar was purged with nitrogen for 10 min. Hexamethyldisilazane (42 mL, 0.20 mol) and THF (78 mL) were charged against positive nitrogen pressure. The addition funnel was charged with a hexane solution of n-butyllithium (78.0 mL, 195 mmol). The amine solution was cooled to −52° C. and n-butyllithium was added over 84 min, resulting in a temperature increase to 12.5° C. over the course of the addition. The resulting lithium hexamethyldisilazide solution was removed from the cooling bath and aged for 30 minutes. To a 500 mL 3-neck round bottom flask equipped with a septum, thermocouple, inert gas inlet and magnetic stir bar was charged 5-chlorobenzoxazole (20.00 g, 130 mmol). The gray solid was dissolved in THF (100 mL) and the resulting colorless solution was cooled to −25° C. The freshly prepared lithium hexamethyldisilazide solution was added via cannula over 80 minutes. The temperature of the anion solution was maintained between −25 and −15° C. during the addition. The resulting dark brown solution was aged for 90 minutes between −25 and −15° C. To a 1000 mL 3-neck round bottom flask equipped with a Claisen adapter, septum, thermocouple, inert gas inlet, stir rod bearing, and blade was charged THF (100 mL) and N-bromosuccinimide (34.8 g, 195 mmol). The resulting slurry was cooled to −20° C. and the anion solution was added via cannula over 150 minutes. During the addition the anion solution and reaction mixture were maintained between −25 and −15° C. The resulting brown slurry was removed from the cooling bath and aged for 50 minutes while warming to room temperature. To the resulting bromide slurry was added a solution of ethanolamine (12.6 mL, 208 mmol) in MeCN (38 mL) via syringe pump over 5 hours. During the addition the reaction temperature was maintained between 20 and 27° C. The resulting brown slurry was aged at room temperature overnight. The reaction mixture was cooled in an ice water bath and the septum replaced with a 50 mL addition funnel charged with concentrated HCl (32 mL, 390 mmol). The acid solution was added over 10 min, during which time the addition the temperature increased from 10 to 20° C. The reaction mixture was removed from the ice water bath and aged for 5 min. A 20% (w/w) solution of $K_2HPO_4$ in water (170 mL) was added and the resulting biphasic mixture was transferred to a seperatory funnel. The flask was washed with THF (3×, 10 mL) and the washings were added. The aqueous phase was cut; the organic phase was washed with 20% (w/w) $K_2HPO_4$ in water (200 mL), separated and analyzed. The crude reaction stream had a total mass of 396.47 g. By quantitative HPLC assayed 25.81 g of 3-3 in the organic phase. $^1$H NMR (500 MHz, DMSO-$d_6$): δ=8.17 (t, J=5.6 Hz, 1H), 7.34 (d, J=8.4 Hz, 1H), 7.25 (d, J=1.8 Hz, 1H), 6.97 (dd, J=8.4, 1.8 Hz, 1H), 4.81 (t, J=5.4 Hz, 1H), 3.56 (q, J=5.7 Hz, 2H), 3.35 ppm (q, J=5.8 Hz, 2H).

Methanesulfonic acid 2-[(5-chloro-benzooxazol-2-yl)-(3-oxo-butyl)-amino]-ethyl ester (3-4)

To a 1000 mL 3-neck round bottom flask equipped with a septum, thermocouple, inert gas inlet and magnetic stir bar was charged 3-3 (25.2 g, 119 mmol). To this flask was added 126 mL DMF, 12.2 mL methyl vinyl ketone (148 mmol) and 0.119 mL 10M NaOH (1.19 mmol). The reaction was then aged for 6 hours, at which time conversion was judged to be complete by HPLC. The solution was diluted with 252 mL iPAc and cooled to 0° C., then 23.1 mL $Et_3N$ (166 mmol) followed by dropwise addition of 12.0 mL methanesulfonyl chloride (154 mmol) over 45 minutes, maintaining internal temperature less than 10° C. After a further 30 minutes, conversion was judged to be complete by HPLC. The solution was washed with 3×63 mL 5 w/w % aqueous $NaHCO_3$ solution, then 66 mL water. After cutting the aqueous layer, the organics were reduced to approximately two volumes or 50 mL iPAc. The organics were then agitated by an overhead stirrer during slow addition of 151 mL n-Heptane over 4 hours. Over this time a crystalline white precipitate developed, and was allowed to stir overnight. At this time there was a thick slurry, which was filtered and washed with 2×50 mL 90:10 n-Heptane:IPAc, and after drying with a nitrogen stream over the filter pad, 3-4 was obtained as a white crystalline solid (34.6 g, 96 mmol). $^1$H NMR (500 MHz, CDCl$_3$): δ=7.29 (s, 1H), 7.16 (d, J=8.2 Hz, 1H), 6.97 (d, J=7.8 Hz, 1H), 4.46 (s, 2H), 3.92 (s, 2H), 3.81 (t, J=5.9 Hz, 2H), 2.98-2.92 (m, 5H), 2.16 (s, 3H).

Example 3

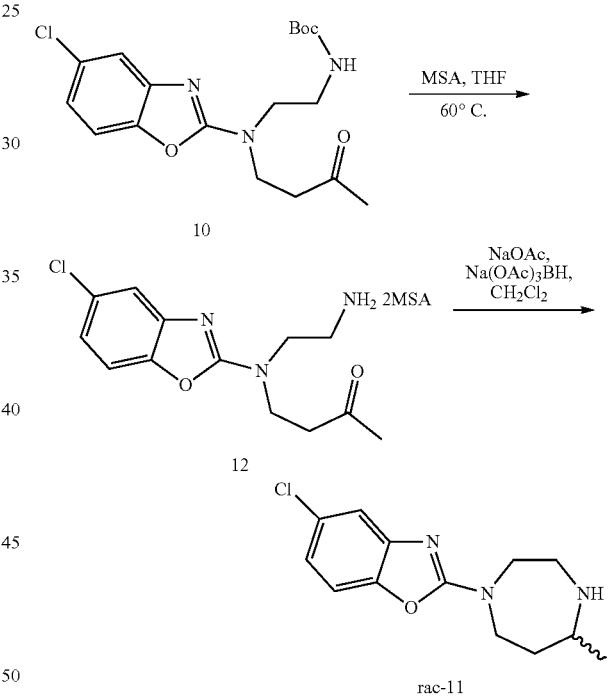

4-[(2-Amino-ethyl)-(5-chloro-benzooxazol-2-yl)-amino]-butan-2-one-bis-MSA salt (12)

MVK adduct 10 (15.04 kg, 39.38 mol) was charged to a vessel and THF (150.4 L) was added. The resulting slurry was cooled to 5° C. and methane sulfonic acid (7.57 kg, 78.8 mol) was added via a diaphragm pump maintaining an internal temperature below 25° C. The batch was heated to 60° C. and allowed to age overnight. After aging overnight HPLC showed the reaction to be 83% complete, thus a further charge of methane sulfonic acid (3.78 kg, 39.3 mol) was added via a diaphragm pump and heating was continued for a further 2 h. It is important to note that charging 3 equiv. of MSA directly to the reaction mixture led to the product oiling out during the course of the reaction. Initially charging 2 equiv. of MSA allowed a seed bed to form which controlled the crystallization during the remainder of the reaction after the final equivalent of MSA had been added. After 2 h HPLC confirmed complete consumption of the starting material. The batch was cooled to 20° C. then filtered and the cake was washed with THF (20 L). The resultant solid was dried in a vacuum oven (T=60° C.) for 36 h, to give 12 (17.4 kg, 36.7 mol) as a pale tan solid. 2% lost to the liquors. m.p. 126.4° C. $^1$H NMR (400 MHz, d$_6$-DMSO): δ 7.86 (bs, 3H), 7.44 (d, 1H, J=8.5 Hz), 7.35 (d, 1H, J=1.1 Hz), 7.06 (dd, 1H, J=8.5 Hz, 1.1 Hz), 3.75 (t, 2H, J=5.6 Hz), 3.69 (t, 2H, J=6.9 Hz), 3.15 (m, 2H), 2.93 (t, 2H, J=5.6 Hz), 2.36 (s, 6H), 2.14 (s, 3H). $^{13}$C NMR (100.6 MHz, d$_6$-DMSO): δ 207.8, 163.1, 147.7, 144.7, 128.6, 120.6, 115.7, 110.6, 46.7, 44.2, 41.3, 40.1 (identified by dept), 37.4, 30.5. HRMS (ESI): m/z [M$^+$+H] calcd for C$_{13}$H$_{16}$ClN$_3$O$_2$: 282.1009; found: 282.1012.

5-Chloro-2-(5-methyl-[1,4]diazepan-1-yl)-benzoxazole (rac-11)

Bis-MSA adduct 12 (17.19 kg, 36.27 mol), sodium acetate (2.97 kg, 36.3 mol) and DCM (152 kg, 115 L) were charged to a vessel. The resulting slurry was cooled to 15° C. and acetic acid (26.8 kg, this was the amount required for dissolution of the salt) was added maintaining an internal temperature below 20° C. The batch was cooled to 15° C. and Na(OAc)$_3$BH (9.25 kg, 43.6 mol) was charged via a glove bag over 30 min maintaining an internal temperature below 20° C. The resulting solution was aged for 30 min at 20° C., HPLC analysis showed the reaction to be complete. The batch was then cooled to 10° C., 2N HCl (38.80 kg) was added and the resulting solution was aged for 30 min at 10° C. The mixture was then adjusted to pH 9 using 5 N NaOH maintaining an internal temperature below 20° C. Once at pH 9 the layers were allowed to separate and the organic lower layer was ran off into a clean drum. DCM (76.2 kg, 57.5 L) was then added to the aqueous phase, the layers were mixed, allowed to separate, then the lower layer was combined with the previous organics (this step was repeated but HPLC of the third DCM layer showed that this was unnecessary as it only contained 12.5 g of rac-11 by assay). The combined DCM fractions were then charged to a 160 liter vessel and distilled to approximately 20 L (~1 volume of DCM). THF (44 kg) was charged to the vessel and the resulting stream was discharged into a clean drum and stored in the cold room prior to the next step in the reaction sequence. The final solution was found to contain 9.4 kg of rac-14. This stream was sufficiently pure to be used directly in the subsequent resolution.

Example 4

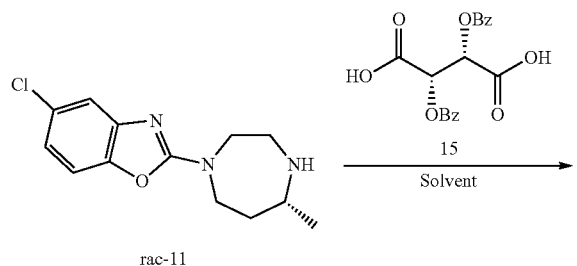

rac-11

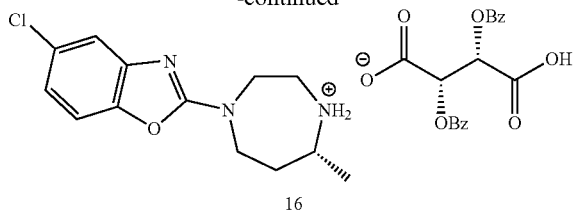

16

DBT Salt (16)

Dibenzoyl-D-tartaric acid 15 (22.6 kg, 63.1 mol) was charged to a vessel. THF (80 kg) was added over 20 min and the suspension stirred (slight exotherm). The amine (9.37 kg, crude from previous step in DCM [~1 vol] and THF [44 kg, 50 L]—total weight 65.5 kg) was added over 35 min (slight exotherm). The solution was seeded with enantiomerically pure 16 (crystallization had already started) and the batch was aged at 20° C. for 4 h analyzing over time by HPLC. The batch showed 72% ee and 35.8 mg/mL liquor loss after 3.5 h. The slurry was filtered (filtration from the vessel took 3 h) and the vessel washed with THF (25 kg), filtering and washing the solid (this filtration took a further 2 h). The solid in the filter was dried with a stream of nitrogen overnight, then dried in a vacuum oven (T=40° C.) for 48 h. The DBT salt 16 (8.47 kg, 13.6 mol) was isolated as a white solid. The liquors after filtration showed 53% ee.

Upgrade of the DBT Salt (16)

The DBT salt 16 (8.35 kg, 13.4 mol, 74% ee) was charged to a vessel. iPAc (137 kg) was added over 10 min and the suspension stirred. MeOH (52 kg) was added over 5 min (slight endotherm), and the batch was aged at 20° C. for 22 h analyzing over time by HPLC. The batch showed 95% ee and 5.3 mg/mL liquor loss after 22 h. The slurry was filtered and the vessel washed with iPAc (29 kg), filtering and washing the solid (total filtration took 1.5 h). The solid was dried in a vacuum oven (T=40° C.) for 20 h. The DBT salt 16 (5.85 kg, 9.37 mol) was isolated as a white solid. The liquors after filtration were 14% ee. m.p. 164.2° C. $^1$H NMR (400 MHz, d$_6$-DMSO): δ 7.93 (d, 4H, J=7.2 Hz), 7.62 (t, 2H, J=7.4 Hz), 7.51̄7.47 (m, 4H), (d, 1H, J=8.0 Hz), 7.34 (d, 1H, J=2.0 Hz), 7.03 (dd, 1H, J=8.4, 2.0 Hz), 5.65 (s, 2H), 3.89̄3.76 (m, 2H), 3.67̄3.58 (m, 1H), 3.43̄3.27 (m, 2H), 3.23̄3.16 (m, 2H), 1.99-1.84 (m, 2H), 1.19̄1.17 (d, 3H, J=6.6 Hz). $^{13}$C NMR (100 MHz, d$_6$-DMSO) δ 168.5, 165.0, 162.4, 147.3, 144.8, 133.4, 129.7, 129.3, 128.7, 128.1, 119.8, 115.3, 109.9, 73.1, 53.5, 44.5, 44.0, 43.8, 31.9, 19.0. HRMS (ESI): m/z [M$^+$+H] calcd for C$_{13}$H$_{16}$ClN$_3$O: 266.1060; found: 266.1058.

Example 5

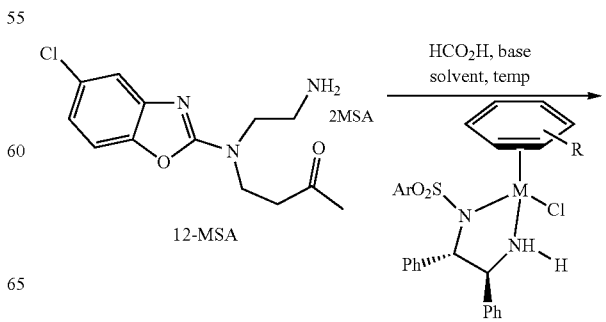

12-MSA

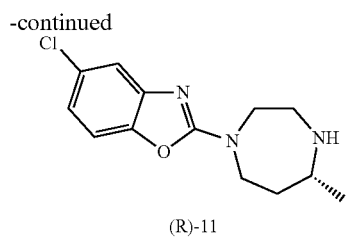

(R)-11

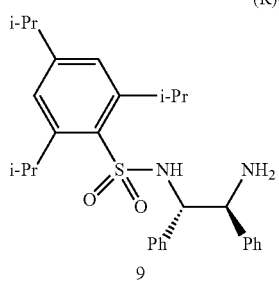

9

(R)-5-Chloro-2-(5-methyl-[1,4]diazepan-1-yl)-benzoxazole (R-11)

Catalyst Preparation: Dichloromethane (6.02 kg), ligand 9 (44 g) and [RuCl$_2$(p-cymene)]$_2$ (28 g) and triethylamine (190 g) were charged to a vessel and stirred to give an orange slurry which was heated to 40° C. for three hours leading to an orange/red solution which was cooled to room temperature. In a second vessel dichloromethane (23 kg) was charged and de-gassed via nitrogen pressure purges. Bis MSA salt 12-MSA (1.46 kg) and anhydrous potassium carbonate powder (325 mesh, 98+%; 1.70 kg) were added followed by deionized water (170 g) maintaining the batch temperature at 15 to 20° C. The vessel contents were then cooled to −10 to −5° C. and aged for 15 minutes, after which time no MSA could be detected in the supernatant, indicating complete salt break had occurred. Triethylamine (780 g) was charged to the mixture maintaining the temperature at −10 to 0° C. followed by the pre-formed catalyst solution, again keeping the temperature between −10 to −5° C. The solution was de-gassed by nitrogen purge and then formic acid (187 g) was added at the same temperature, leading to formation of a thick slurry. This was followed by a second formic acid charge of 380 g after 30 minutes. The reaction temperature was maintained at −10 to −5° C. and the mixture aged for 16 hours. The reaction was quenched by addition of NaOH solution (18 kg, 1.0 M, aq.) maintaining the temperature below 0° C., confirmed to have a pH>11 and allowed to warm to room temperature. The bi-phasic mixture was stirred vigorously, the layers allowed to separate and the lower organic layer collected. The organic layer was then concentrated to low volume and solvent switched to toluene, distilling until a final volume of about 4 L was reached with <0.05 vol % DCM remaining. The solution was filtered (to remove any residual solids) and the filter washed with 1.5 kg of toluene. DMAc (2.2 kg) was added and the solvent ratio checked by GC of NMR to allow for accurate addition of more solvent to ensure a final volumetric ratio of 33% DMAc and 67% toluene. Additional toluene (approx 6 kg) and DMAc (approx 3.4 kg) were added followed by anhydrous HCl (220 g) over 45 minutes maintaining the batch temperature at 15 to 25° C. and the batch seeded with a previously prepared sample of HCl salt. Additional HCl (110 g) was added over 4 hours at the same temperature, de-gassed by nitrogen purges and sampled to ensure a pH<4.

The salt was then cooled to 0° C. over 3 hours, the supernatant checked to confirm acceptable losses and the solids isolated by filtration and washed with about 1.0 kg of toluene. The solids were dried at 40° C. to afford 802 g of amine HCl salt (R)-11-HCl, 87% yield, >99.9% purity and 99.7% ee.

Analytical data for 11 and a (free bases). 11 $^1$H NMR (500 MHz, CD$_2$Cl$_2$) δ 7.22 (d, J=2.1 Hz, 1H), 7.146 (d, J=8.2 Hz, 1H), 6.93 (dd, J=8.4, 2.6 Hz, 1H), 3.90 (ddd, J=14.5, 6.1, 4.1 Hz, 1H), 3.80 (dt, J=13.7, 3.3 Hz, 1H), 3.68-3.56 (m, 2H), 3.20 (dt, J=14.2, 3.5 Hz, 1H), 2.92 (ddd, J=14.2 Hz, 11.0, 3.5 Hz, 1H), 2.77 (dqd, J=9.9, 6.4, 3.3 Hz, 1H), 1.94 (ddt, J=14.3, 6.0, 3.2 Hz, 1H), 1.59-1.46 (m, 2H), 1.10 (d, J=6.4 Hz, 3H); $^{13}$C NMR (126 MHz, CD$_2$Cl$_2$) δ 164.10, 148.30, 146.06, 129.39, 119.97, 116.09, 109.55, 55.76, 51.68, 48.13, 46.59, 38.40, 23.58; LCMS: [M+H]$^+$ calcd for C$_{13}$H$_{16}$ClN$_3$O+H$^+$, 266.1; found 265.9.

a (Obtained as a 39:61 mixture with 3). $^1$H NMR (500 MHz, CD$_2$Cl$_2$) δ 7.22 (d, J=2.1 Hz, 1H), 7.151 (d, J=8.4 Hz, 1H), 6.93 (dd, J=8.4, 2.6 Hz, 1H), 4.32 (d of quintet, J=12.0, 6.0 Hz, 1H), 4.03 (dd, J=15.4, 2.4 Hz, 1H), 3.28 (ddd, J=14.8, 10.4, 1.3 Hz, 1H), 3.12-3.02 (m, 2H), 2.83 (ddd, J=11.9, 10.9, 1.4 Hz, 1H), 2.56 (dd, J=14.0, 10.0 Hz, 1H), 2.22 (dt, J=15.3, 6.7 Hz, 1H), 1.65 (dtd, J=15.3, 10.0, 1.2 Hz, 1H), 1.26 (d, J=6.5 Hz, 1H). $^{13}$C NMR (126 MHz, CD$_2$Cl$_2$) δ 164.01, 148.30, 148.24, 146.05 (coincident), 129.39 (coincident), 119.93, 116.02, 109.53, 53.93, 50.15, 47.12, 46.89, 40.23 19.97. LCMS: [M+H]$^1$ calcd for C$_{13}$H$_{16}$ClN$_3$O+H$^+$, 266.1; found 265.9.

Example 6

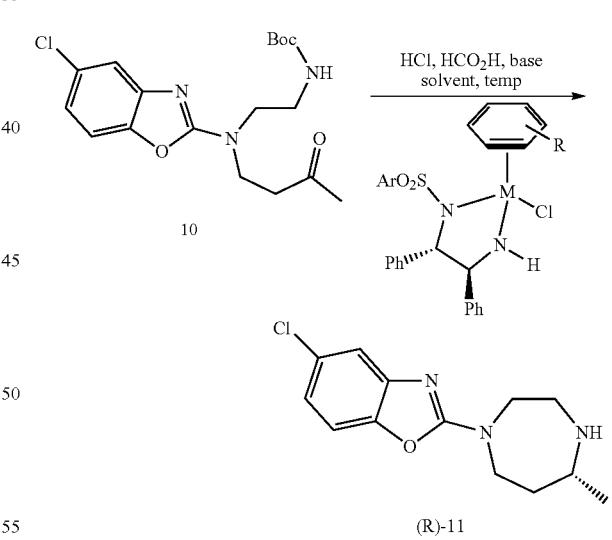

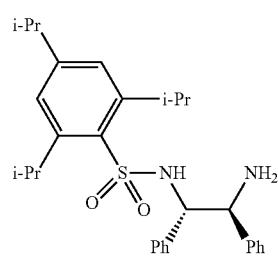

9

(R)-5-Chloro-2-(5-methyl-[1,4]diazepan-1-yl)-benzoxazole (R-11)

Catalyst Preparation: A pressure flask was charged with Ligand (9) (2.41 g, 5.02 mmole), ruthenium cymene dichloride dimer (1.54 g, 2.51 mmole), triethylamine (1.01 g, 10.04 mmole), and acetonitrile (144.5 mls). The solution was heated to 80 C for 2 hr then cooled to ambient and stored 145.0 mls of solution in inert environment.

A reactor was charged with 2N HCl solution (52.4 mls). To this was then charged MVK adduct (10 g, 26.2 mmol) in 4 separate additions of 2.5 g each. At 20C the reaction was stirred for 4 hrs then heated the slurry to 30 C for an additional 6 hrs and defined conversion. No starting MVK adduct was present following 6 hrs at 30 C, and began neutralization of the hydrochloride salt by charging 100 mls of toluene to the reactor. Then to this charge, added 50% potassium phosphate tribasic (66.8 g, 157 mmol), checked pH to ensure that it was greater than 10 and proceeded to warm batch to 35° C. Phase separated the toluene layer and back extracted the aqueous layer with an additional 25 mls of toluene, then again phase separated and combined the toluene layers. Distilled the toluene to azeotropically dry system down to 60 mls total of solution.

Took 20 mls of the above forementioned toluene solution or 8.72 mmoles based on MVK adduct charged and to it charged 13.3 mls of toluene and 28.3 mls of acetonitrile. Cooled the reaction solution down to −5 C. To the reaction vessel then charged triethylamine (0.882 g, 8.72 mmole). Then to this charged previous prepared ruthenium catalyst (0.1744 mmole). To the vessel then charged formic acid (0.401 g, 8.72 mmole) while maintaining temperature at −5 C. Once feed of formic acid was complete, started 24 hr age of batch. During this age charged formic acid (0.802 g, 17.44 mmole) and began purging vessel with nitrogen. After 24 hrs determined the conversion and ee of reaction by LC. (98.4% conv, 94.2% ee)

Example 7 and mixture cooled to RT. Aqueous 3.6 M HCl (36 L) was added (exotherm) and the mixture extracted twice with ethyl acetate (2×30 L). The combined organics were washed with LiCl solution (2×20 L). The acid solution assayed for 3.79 kg of 5 (81%) and 4.64 kg of 5 and 20 combined (99%).

A solution of acids 5 and 20 (approx. 4.64 kg, 22.9 mol) in THF and EtOAc (approx. 110 L) was concentrated to low volume. THF (90 L) was added and the solvent composition checked by NMR to ensure most ethyl acetate had been removed. Sodium tert-butoxide (2.42 kg, 25.2 mol) was added slowly as a solid over 1-2 h (slight exotherm), allowing the sodium salt to form and stirred overnight at RT. The liquors showed a 45:55 ratio of product 5: starting material 19 and the solid was collected by filtration, washed with THF (2×20 L) and dried in a vacuum oven (T=40° C.) for 15 h to afford 4.22 kg of crude sodium salt. The crude sodium salt (4.22 kg, 14.9 mol) was charged to a 50 L vessel and 3.6 M HCl (21.2 L) was added with cooling. The slurry was then stirred at room temperature for 16 h and the off-white solid isolated by filtration. The cake was washed with water (11 L) and iPAc/Heptane (2×5 L), then dried in a vacuum oven (T=35° C.) for 15 h to give 3.10 kg of crude acid 5 (97.9 LCAP, 92 wt %, corrected weight 2.85 kg, 61% yield from 19). The acid 5 (2.85 kg corrected, 14.0 mol) was charged to a 50 L vessel and EtOAc (28 L) and dilute 0.22 M HCl (14 L) were added and the mixture stirred until two clear phases resulted. The aqueous layer was removed and the organic layer filtered to remove any particulate matter. The ethyl acetate was reduced to about 8 L and then heptane (15.6 L) was added over 1 h and the liquors sampled to check for appropriate losses. The solid was isolated by filtration, washed with heptane:ethyl acetate (3:1, 4 L) and dried on the filter under nitrogen to give 2.81 kg of acid 5. m.p. 167.5° C. $^1$H NMR (400 MHz, $d_6$-DMSO): δ 12.09 (br s, 1H), 8.04 (s, 1H), 7.62 (d, 1H, J=8.4 Hz), 7.58 (d, 1H, J=1.2 Hz), 7.49 (dd, 1H, J=8.4, 1.2 Hz), 2.41 (s, 3H). $^{13}$C NMR (100.6 MHz, $d_6$-DMSO): δ 168.0, 139.2, 136.4, 135.8, 132.5, 130.3, 128.7, 124.8, 20.9. HRMS (ESI): m/z [M$^+$+H] calcd for $C_{10}H_9N_3O_2$: 204.0773; found: 204.0781.

Example 8

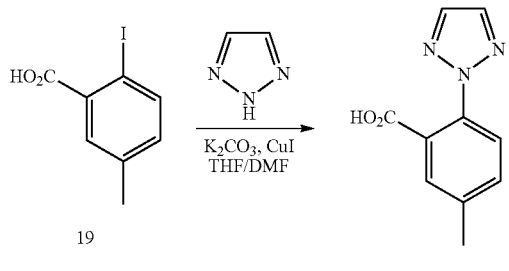

5-Methyl-2-[1,2,3]triazol-2-yl-benzoic acid (5)

The iodide 19 (6.04 kg, 23.0 mol), THF (45 L) and DMF (9.0 L) were charged to a vessel. Copper iodide (218 g, 1.15 mol) and potassium carbonate (7.94 kg, 57.4 mol) were added and the mixture heated to an internal temperature of 40° C. 1,2,3-Triazole (3.16 kg, 46.0 mol) was added as a solution in THF (6.0 L) over half an hour (no exotherm) and heating continued to 65° C. (again no exotherm observed) and the reaction monitored by HPLC. Once complete N,N-dimethylethylenediamine (244 mL, 2.30 mol) was added

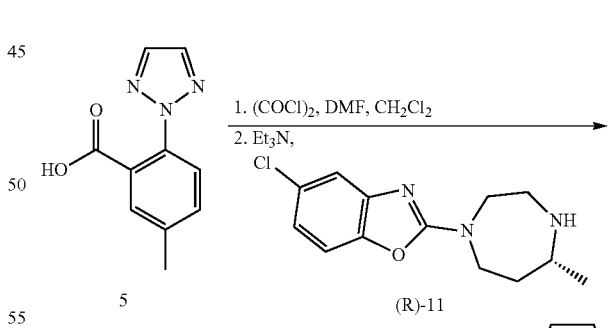

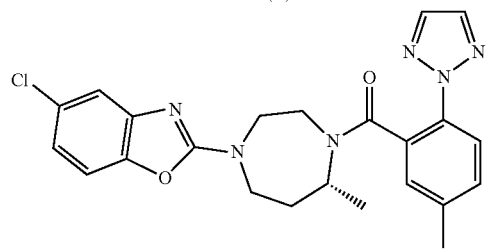

[(R)-4-(5-Chloro-benzooxazol-2-yl)-7-methyl-[1,4]diazepan-1-yl]-(5-methyl-2-[1,2,3]triazol-2-yl-phenyl)-methanone (1)

The amine DBT salt 16 (5.67 kg, 9.09 mol) was charged to a vessel and inerted. DCM (28 L) was added, followed by 4 N Sodium Hydroxide solution (prepared from 10 N NaOH [22.4 L] and water [36 L]). The slurry was then stirred at ambient temperature for 1 h until a solution was obtained. The layers were separated and the aqueous phase treated with sodium chloride solution (10.1 kg in 20 L water). DCM (5 L) was then added and the bi-phasic mixture stirred for 10 min before separating the layers. The combined organic layers were then concentrated under reduced pressure to a 10 L volume. The solution of the free amine was used directly in the next reaction.

The triazole acid 5 (13.25 kg, 65.2 mol), DCM (88 L) and DMF (1.35 L, 17.4 mol) were charged to a vessel and the resulting suspension was cooled to 0° C. Oxalyl chloride (8.28 kg, 65.2 mol) was added portion wise keeping the internal temperature between 5 and 10° C. (the anhydride formed above 10° C.), then the reaction was aged for 30 min at this temperature. HPLC analysis showed acid 5 remained; an additional charge of oxalyl chloride (160 g, 1.26 mol) was made, and the solution stirred at 5° C. for 30 minutes. A solution of the amine (R)-11 (16.5 kg, 62.1 mol) and triethylamine (13.19 kg, 130.0 mol) in DCM (~8 L) was added to the acid chloride over 30 minutes, keeping the internal temperature less than 15° C. The resulting slurry was aged for 30 minutes and then quenched by the addition of water (167 L) over 10 minutes, keeping the internal temperature <15° C. The lower organic layer was removed, and then concentrated under atmospheric pressure to a volume of 100 L. Assay at this stage showed 27.3 kg 1, 98%. The solution was solvent switched to MeCN (ca. 560 L, 20 mL/g) by distillation under reduced pressure at <50° C. The MeCN solution was treated with ecosorb C-941 (2.8 kg) slurried in MeCN (10 L). The resulting slurry was aged for 30 min then filtered through a Solka Flok pad and a 0.1 um cartridge filter washing with MeCN (2×30 L). The MeCN filtrate was concentrated under reduced pressure at <50° C. to a final volume of ca 112 L. The slurry was cooled to 25° C. and water (280 L) added over 40 minutes. The resulting slurry was aged at 20° C. for 1 hour, then filtered, washing the cake with 5:1 water: MeCN (60 L) followed by water (40 L). The solid was dried in the vacuum oven with nitrogen purge overnight at 50° C. The final target 1 was isolated as a white solid, 26.72 kg, 95%, 98.5% ee, 99.6 LCAP. m.p. 153.1° C. $[\alpha]_D^{25}$ −11.8 (c 1.0, MeOH) for a sample of 97.8% ee. HRMS (ESI): m/z [M++H] calcd for $C_{23}H_{23}ClN_6O_2$: 451.1649; found: 451.1640.

Example 9

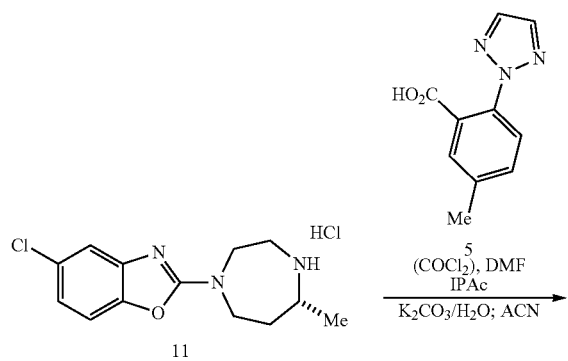

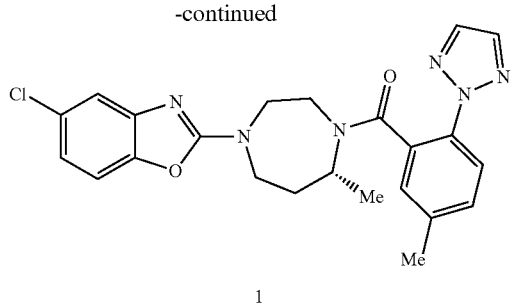

[(R)-4-(5-Chloro-benzooxazol-2-yl)-7-methyl-[1,4]diazepan-1-yl]-(5-methyl-2-[1,2,3]triazol-2-yl-phenyl)-methanone (1)

A round bottom flask was charged 6.86 g of 5-methyl-2-[1,2,3]triazol-2-yl-benzoic acid (5) along with 7.0 vol or 70 mls of dry iPAc (KF<200 ppm) forming a slurry. To this was charged 0.73 g of DMF then the system was purged thoroughly with nitrogen and temperature was set at 20° C.-25° C. 5.04 g of oxalyl chloride was added while maintaining 20° C.-25° C. and controlling off-gassing since it is extremely vigorous. With the feed of oxalyl chloride the previous slurry dissolved. The batch was aged for 1 hr, sampled for acid chloride formation (<1 LCAP) and allowed to proceed to amidation. In a separate vessel a solution of potassium carbonate was prepared in 5.0 vol or 50 mL water (note: exotherm). The solution was cooled to 0° C. When acid chloride (above) was prepared, added 2.5 vol or 25 mL iPAc to the aqueous solution with overhead stirring, then added 10.0 g. amine hydrochloride salt (11) to solution, and stirred for 15 minutes. Then using a cannula, the acid chloride solution was transferred over from separate vessel over the course of 1 hour, maintaining less than 5° C. internal temperature. The vessel was flushed with 2.5 vol or 25 mL iPAc and sampled to determine completion. The slurry was heated to 40° C. Upon reaching 40° C., 1.5 vol or 15 mL Acetonitrile was and agitated for 5 minutes, and all material went into solution (98% AY observed). Agitation was stopped. After phase separation, the aqueous layer was cut, the organics were stirred with DARCO (10 wt % 6 basis) at 40° C. for 3 hours, then filtered hot and taken through to crystallization. Additional product was recovered from the carbon with an iPAc flush.

The batch was concentrated in iPAc and flushed to 7.5 vol (L/Kg of 1) and heated to 80-85C until complete dissolution. The solution was cooled to 65° C. linearly over 2 hrs, and the agitation speed was adjusted to high. At 65° C., the solution was charged with 0.3 wt % seed in n-Heptane and aged for 1 hour. After the age and confirmation of the seedbed, the batch was cooled to 45° C. over 2.5 hrs. At this time a solvent switch was conducted at constant volume to a ratio of 90:10 n-Heptane:iPAc. The material was filtered hot at 45° C., the cake was washed with 3 vol (L/Kg of 1) of 90:10 n-Heptane:iPAc twice, followed by 3 vol (L/Kg of 1) of n-Heptane twice. The cake was dried at 70° C. under vacuum to give 14.4 g. 1 (31.8 mmol) as a crystalline white powder.

Example 10

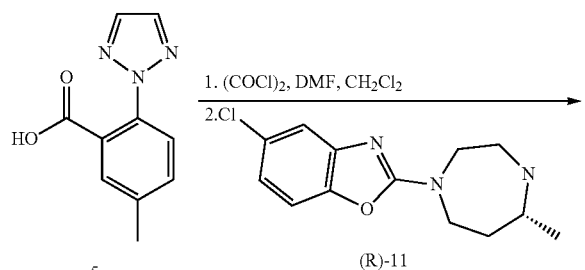

3. Et₃N
4. H₂O
5. Carbon Treatment
6. Seed
7. Solvent switch to IPAcn-Hepatne
8. IKA Milling

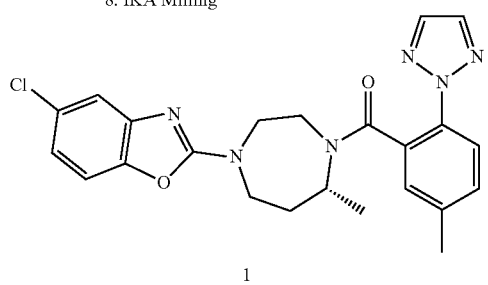

[(R)-4-(5-Chloro-benzooxazol-2-yl)-7-methyl-[1,4]diazepan-1-yl]-(5-methyl-2-[1,2,3]triazol-2-yl-phenyl)-methanone (1)

A reaction vessel was charged with 213.4 g of triazole acid (5) along with 7.4 vol or 2236 mls of dry iPAc (KF<200 ppm) forming a slurry. To this charge was added 21.93 g of DMF then the system was purged thoroughly with nitrogen and temperature was maintained at 20-25 C. Charged 152.3 g of oxalyl chloride while maintaining 20-25C and control of off-gassing since it is extremely vigorous. With the feed of oxalyl chloride the previous slurry all dissolved. The batch was aged for 1 hr. The reaction was sampled for Acid Chloride formation (<1 LCAP) and proceeded to distillation. Distillation was conducted down to 1118 mls or constant volume distillation using 7.4 vol of fresh iPAc under vacuum maintaining less than 30° C.

In a separate vessel prepared a solution of 302.2 g of amine hydrochloride salt (11) in 15.3 vol or 4624 mls of dry iPAc (KF<200 ppm) to form a slurry. Then transferred the acid chloride solution using a cannula over from a separate vessel followed by flushing the vessel with 6.9 vol or 2085 mls of iPAc. With the amine and acid chloride in the same vessel began addition of 404.8 g of triethylamine. This charge was made over 1 to 4 hrs at a temperature between 20-40C with a desired control of the temperature between 20-30 C. Once feed of the TEA was complete, the batch was aged for 1 hr and then sampled to determine completion.

Once the batch was complete, charged 7.4 vol of water or 2236 mls and then heated the solution to 40 C. Once at 40 C, the mixture was aged 5 minutes then stopped agitation. The phases separated but there was an appreciable rag layer so it was allowed to settle and cut the rag was along with the aqueous layer. The aqueous rag was filtered then back extracted the aqueous layer with 3.5 vol or 1058 mls of iPAc and combined all iPAc layers.

The batch was recycled in iPAc (~60 g per kg of iPAc) via a Cuno filter (1 bundle per 39 Kg Amine HCl Salt) for several hours at 40° C. The batch was drummed off through a sparkler filter and recovered additional material from the carbon with an iPAc flush.

The batch was concentrated in iPAc and flushed to 7.5 vol (L/Kg of product) and heated to 80-85° C. until complete dissolution. The mixture was cooled to 65° C. linearly over 2 hrs, and agitation speed was adjusted to high from this point forward. At 65° C., the mixture was charged with 0.3 wt % of [(R)-4-(5-chloro-benzooxazol-2-yl)-7-methyl-[1,4]diazepan-1-yl]-(5-methyl-2-[1,2,3]triazol-2-yl-phenyl)-methanone seed in n-Heptane and aged for 1-3 hours. After the age and confirmation of the seed bed, the batch was cooled to 45° C. over 2.5 hrs. A solvent switch was conducted at constant volume to a ratio of 90:10 n-Heptane:iPAc.

The batch was wet milled to a uniform particle size and filter hot at 45° C. The cake was washed with 3 vol (L/Kg of product) of 90:10 n-Heptane:iPAc twice, followed by 3 vol (L/Kg of product) of n-heptane twice. The cake was dried at 70° C. under vacuum.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound which is:

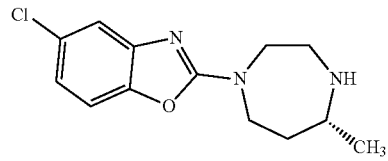

or a salt thereof.

2. The compound of claim 1 which is:

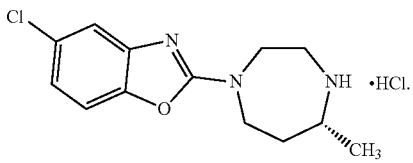 [SMILES: C[C@@H]1CCN(c2nc3cc(Cl)ccc3o2)CCN1]

3. A compound which is:

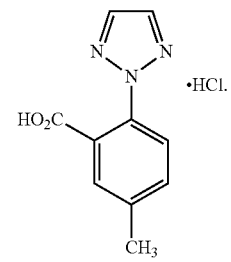

* * * * *

UNITED STATES PATENT AND TRADEMARK OFFICE
CERTIFICATE OF CORRECTION

PATENT NO. : 11,401,266 B2
APPLICATION NO. : 14/801424
DATED : August 2, 2022
INVENTOR(S) : Carl A. Baxter and Faye Sheen It is certified that error appears in the above-identified patent and that said Letters Patent is hereby corrected as shown below:

On the Title Page

Item (71) The Applicant should be reflected as follows:
Merck Sharp & Dohme (UK) LIMITED
London, UNITED KINGDOM Signed and Sealed this
Twenty-sixth Day of September, 2023

Katherine Kelly Vidal
*Director of the United States Patent and Trademark Office*